US007655043B2

United States Patent
Peterman et al.

(10) Patent No.: US 7,655,043 B2
(45) Date of Patent: Feb. 2, 2010

(54) EXPANDABLE SPINAL IMPLANT AND ASSOCIATED INSTRUMENTATION

(75) Inventors: Marc M. Peterman, Memphis, TN (US); Jeffrey D. Moore, Olive Branch, MS (US); Paul Tucker Geibel, San Antonio, TX (US)

(73) Assignee: Warsaw Orthopedic, Inc.

( * ) Notice: Subject to any disclaimer, the term of this patent is extended or adjusted under 35 U.S.C. 154(b) by 200 days.

(21) Appl. No.: 11/117,890

(22) Filed: Apr. 29, 2005

(65) Prior Publication Data

US 2006/0247771 A1 Nov. 2, 2006

(51) Int. Cl.
*A61F 2/44* (2006.01)

(52) U.S. Cl. .................................... 623/17.11

(58) Field of Classification Search ............ 606/57, 606/61, 72, 90, 232; 623/13.15, 17.11, 17.15, 623/17.16, 23.47
See application file for complete search history.

(56) References Cited

U.S. PATENT DOCUMENTS

| 4,863,476 | A | | 9/1989 | Shepperd |
| 5,059,193 | A | * | 10/1991 | Kuslich ................. 606/61 |
| 5,390,683 | A | * | 2/1995 | Pisharodi ................ 128/898 |
| 5,522,899 | A | | 6/1996 | Michelson |
| 5,554,191 | A | | 9/1996 | Lahille et al. |
| 5,609,635 | A | | 3/1997 | Michelson |
| 5,653,763 | A | | 8/1997 | Errico et al. |
| 5,658,335 | A | | 8/1997 | Allen |
| 5,665,122 | A | | 9/1997 | Kambin |
| 5,776,199 | A | | 7/1998 | Michelson |
| 5,782,832 | A | | 7/1998 | Larsen et al. |
| 6,080,193 | A | | 6/2000 | Hochshuler et al. |
| 6,102,950 | A | | 8/2000 | Vaccaro |
| 6,117,174 | A | | 9/2000 | Nolan |
| 6,129,763 | A | | 10/2000 | Chauvin et al. |
| 6,176,882 | B1 | * | 1/2001 | Biedermann et al. ..... 623/17.15 |
| 6,179,873 | B1 | | 1/2001 | Zientek |
| 6,190,414 | B1 | | 2/2001 | Young et al. |
| 6,371,989 | B1 | | 4/2002 | Chauvin et al. |

(Continued)

FOREIGN PATENT DOCUMENTS

DE 44 16 605 C1 6/1995

(Continued)

OTHER PUBLICATIONS

Coda, http://www.spinalconcepts.com/products/code.html, Jun. 8, 2005, Copyright 2004 Spinal Concepts, 1 page.

*Primary Examiner*—Thomas C Barrett
*Assistant Examiner*—Nicholas Woodall

(57) ABSTRACT

An expandable spinal implant including an implant body transitionable between an initial configuration and an expanded configuration. The implant body includes first and second axial walls spaced apart along a transverse axis, with at least one of the walls including first and second axial wall portions laterally offset from one another. An expansion member co-acts with the first wall portion to outwardly displace the first wall portion relative to the second wall portion to transition the implant body to the expanded configuration. In another embodiment, the first wall portion defines a recessed region relative to the second wall portion when the implant body is in the initial configuration, and wherein the recessed region is outwardly expanded as the implant body is transitioned to the expanded configuration. In a further embodiment, the first wall portion is movable while the second wall portion remains substantially stationary.

45 Claims, 6 Drawing Sheets

U.S. PATENT DOCUMENTS

| | | |
|---|---|---|
| 6,436,140 B1 | 8/2002 | Liu et al. |
| 6,610,089 B1 | 8/2003 | Liu et al. |
| 6,955,691 B2 * | 10/2005 | Chae et al. ............... 623/17.16 |
| 7,074,240 B2 * | 7/2006 | Pisharodi ................. 623/17.15 |
| 7,220,280 B2 * | 5/2007 | Kast et al. ................ 623/17.11 |
| 2002/0040243 A1 | 4/2002 | Attali et al. |
| 2004/0267361 A1 * | 12/2004 | Donnelly et al. ......... 623/13.14 |
| 2006/0058878 A1 * | 3/2006 | Michelson ............... 623/17.11 |

FOREIGN PATENT DOCUMENTS

| | | |
|---|---|---|
| EP | 1 415 622 | 9/2003 |
| WO | WO 92/14423 | 9/1992 |
| WO | WO 97/00054 | 1/1997 |
| WO | WO 00/12033 | 3/2000 |
| WO | WO 01/68005 | 9/2001 |

\* cited by examiner

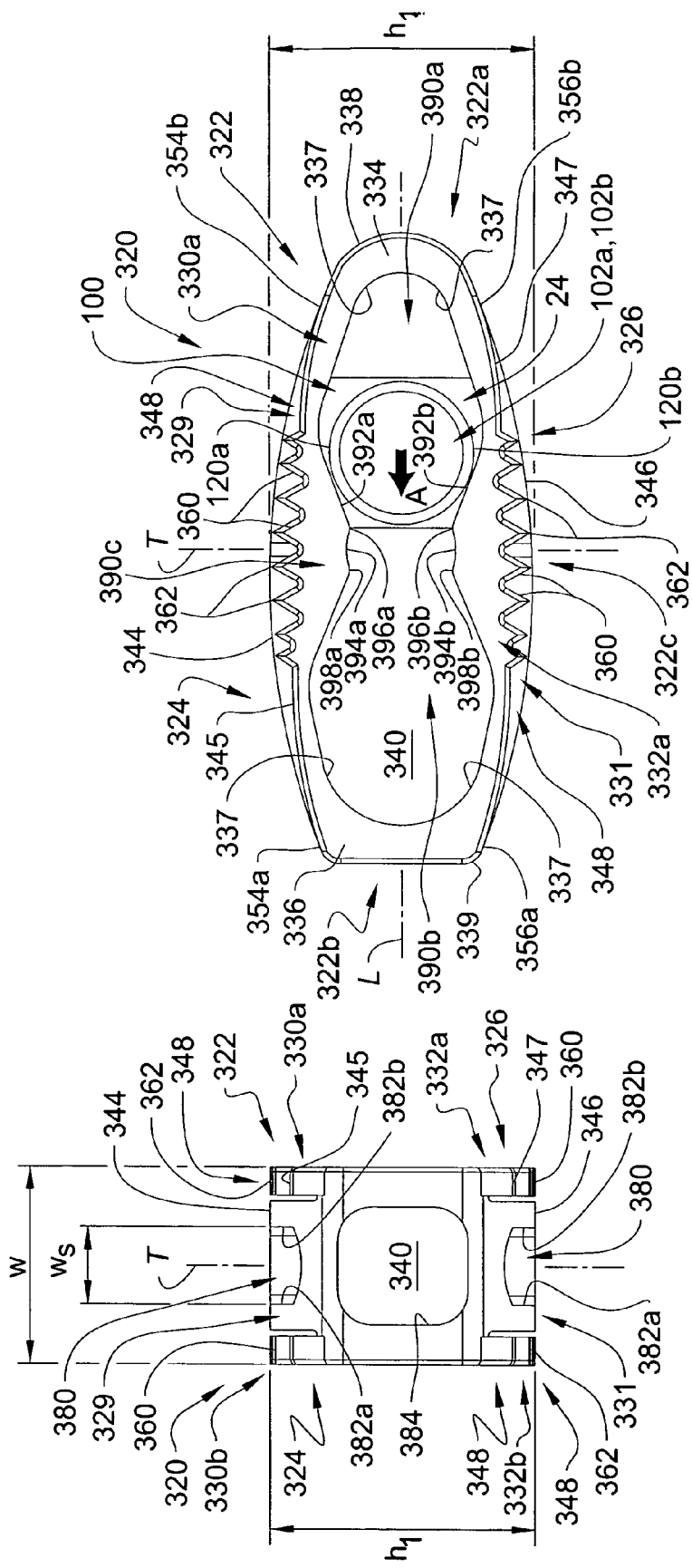

EXPANDABLE SPINAL IMPLANT AND ASSOCIATED INSTRUMENTATION

CROSS REFERENCE TO RELATED APPLICATIONS

The subject patent application is related to a U.S. Patent Application entitled "Expandable Intervertebral Implant and Associated Instrumentation" filed on the same day as the subject patent application, the contents of which are hereby incorporated by reference.

FIELD OF THE INVENTION

The present invention relates generally to the field of spinal implants, and more particularly relates to an expandable spinal implant and associated instrumentation.

BACKGROUND

There have been numerous attempts to develop intervertebral implants to replace a damaged or degenerated natural spinal disc and to maintain sufficient stability of the disc space between adjacent vertebrae, at least until arthrodesis is achieved. Intervertebral implants can either be solid, sometimes referred to as a spacer or plug, or can define a hollow interior designed to permit bone in-growth, sometimes referred to as a fusion device or fusion cage. The interior of a fusion device may be filled with a bone growth inducing substance to facilitate or promote bone growth into and through the device to achieve a more rapid and stable arthrodesis.

Various types, shapes and configurations of intervertebral implants are known in the art. For example, one of the more prevalent designs includes intervertebral implants having a cylindrical shape and defining external threads to facilitate insertion into the disc space. As a result, reaming and tapping of the adjacent vertebral bodies is required to form a threaded passage for receiving the threaded implant. However, these techniques generally involve over-reaming of the posterior portion of the adjacent vertebral bodies, thereby resulting in excessive removal of load bearing vertebral bone which may lead to instability of the portion of the spinal column being treated. Other types of intervertebral implants have a generally rectangular configuration having planar upper and lower outer surfaces for engagement with adjacent vertebral bodies. However, the planar upper and lower outer surfaces may not adequately conform to the shape of the vertebral endplates, thereby resulting in non-uniform and inconsistent engagement between the implant and the adjacent vertebral bodies.

Additionally, most intervertebral implant designs have a predetermined, fixed height that approximates the natural height of the disc space. Insertion of an intervertebral implant having a fixed height usually requires distraction of the disc space to an insertion height somewhat greater than the natural height of the disc space. Attempts have also been made to develop various types of expandable intervertebral implants that are configured to expand along the height of the disc space. These types of expandable implants typically include multiple arms or branches having proximal end portions that extend from a fixed base, and distal end portions that remain unconnected and free to move independently of one another. A wedge is displaced between the arms to separate or splay the distal end portions of the arms apart to transition the implant to an expanded configuration defining a taper and having a maximum implant height adjacent the distal end portion of the implant. Notably, positioning of the wedge adjacent the distal end portions of the arms fails to provide support along the mid-portion of the implant to resist compression forces exerted onto the implant by the adjacent vertebral bodies. Additionally, the expansion wedge may occupy a significant portion of the inner chamber of the implant, thereby reducing the capacity of the implant to receive bone growth inducing material therein.

Moreover, some intervertebral implant designs include upper and lower bearing surfaces that are engaged against upper and lower vertebral endplates to maintain a select disc space height. These implants sometimes include teeth or other types of surface projections extending from the upper and lower bearing surfaces to aid in gripping the adjacent vertebral endplates to substantially prevent migration of the implant and possible expulsion of the implant from the disc space. However, the inclusion of teeth or other types of surface projections increases the overall height of the implant. As a result, the adjacent vertebrae must be spread apart a distance sufficient to establish a disc space height that is at least as great as the overall height of the implant, including the height of the teeth. Spreading the adjacent vertebrae apart to accommodate for the overall height of the implant may result in over distraction of the disc space. Additionally, insertion of the implant into the disc space may be impeded by the teeth or other surface projections that extend beyond the upper and lower bearing surfaces.

Thus, there is a general need in the industry to provide an improved expandable spinal implant and associated instrumentation. The present invention satisfies this need and provides other benefits and advantages in a novel and unobvious manner.

SUMMARY

The present invention relates generally to an expandable spinal implant and associated instrumentation. While the actual nature of the invention covered herein can only be determined with reference to the claims appended hereto, certain forms of the invention that are characteristic of the preferred embodiments disclosed herein are described briefly as follows.

In one form of the present invention, an expandable spinal implant is provided, including an implant body having a longitudinal axis and being transitionable between an initial configuration and an expanded configuration, with the implant body including first and second axial walls spaced apart along a transverse axis, and with at least one of the axial walls including first and second axial wall portions laterally offset from one another. The implant further includes an expansion member that co-acts with the first wall portion to outwardly displace the first wall portion relative to the second wall portion generally along the transverse axis to transition the implant body from the initial configuration to the expanded configuration.

In another form of the present invention, an expandable spinal implant is provided, including an implant body having a longitudinal axis and being transitionable between an initial configuration and an expanded configuration, with the implant body including first and second axial walls spaced apart along a transverse axis, and with at least one of the axial walls including first and second axial wall portions laterally offset from one another. The first wall portion defines a recessed region relative to the second wall portion when the implant body is in the initial configuration. The implant further includes an expansion member that co-acts with the first wall portion to transition the implant body from the initial configuration to the expanded configuration wherein the recessed region is outwardly expanded generally along the transverse axis.

In another form of the present invention, an expandable spinal implant is provided, including an implant body having a longitudinal axis and being transitionable between an initial configuration and an expanded configuration, with the implant body including first and second axial walls spaced apart along a transverse axis, and with at least one of the axial walls including a movable wall portion and a substantially stationary wall portion laterally offset from one another. The implant further includes an expansion member that co-acts with the movable wall portion to outwardly displace the movable wall portion relative to the stationary wall portion generally along the transverse axis to transition the implant body from the initial configuration to the expanded configuration.

It is one object of the present invention to provide an improved expandable spinal implant and associated instrumentation. Further objects, features, advantages, benefits, and aspects of the present invention will become apparent from the drawings and description contained herein.

BRIEF DESCRIPTION OF THE DRAWINGS

FIG. 10 is a side elevational view of an expandable spinal implant according to another form of the present invention, as shown in an initial, non-expanded state.

FIG. 11 is an end elevational view of the expandable spinal implant illustrated in FIG. 10, as shown in the initial, non-expanded state.

DESCRIPTION OF THE PREFERRED EMBODIMENTS

Figure 1:
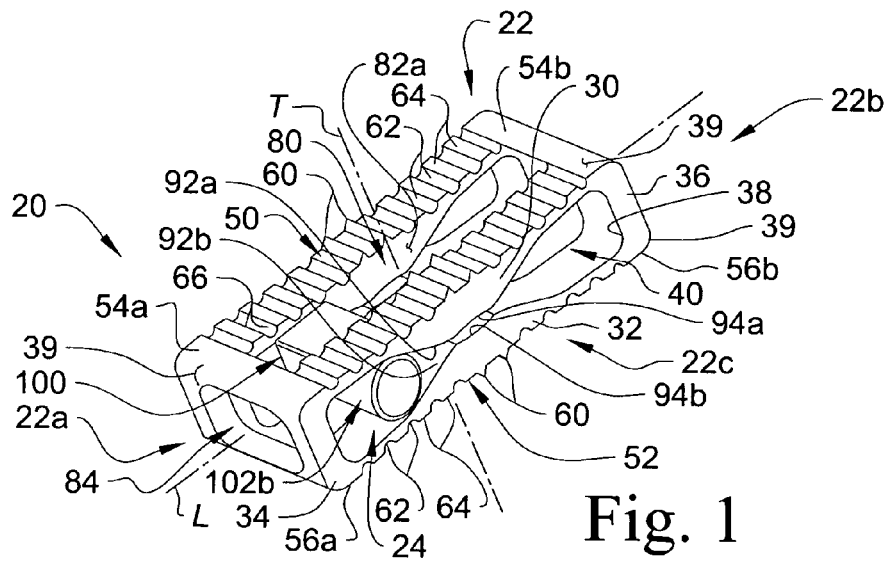
FIG. 1 is a perspective view of an expandable intervertebral implant according to one form of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 7:
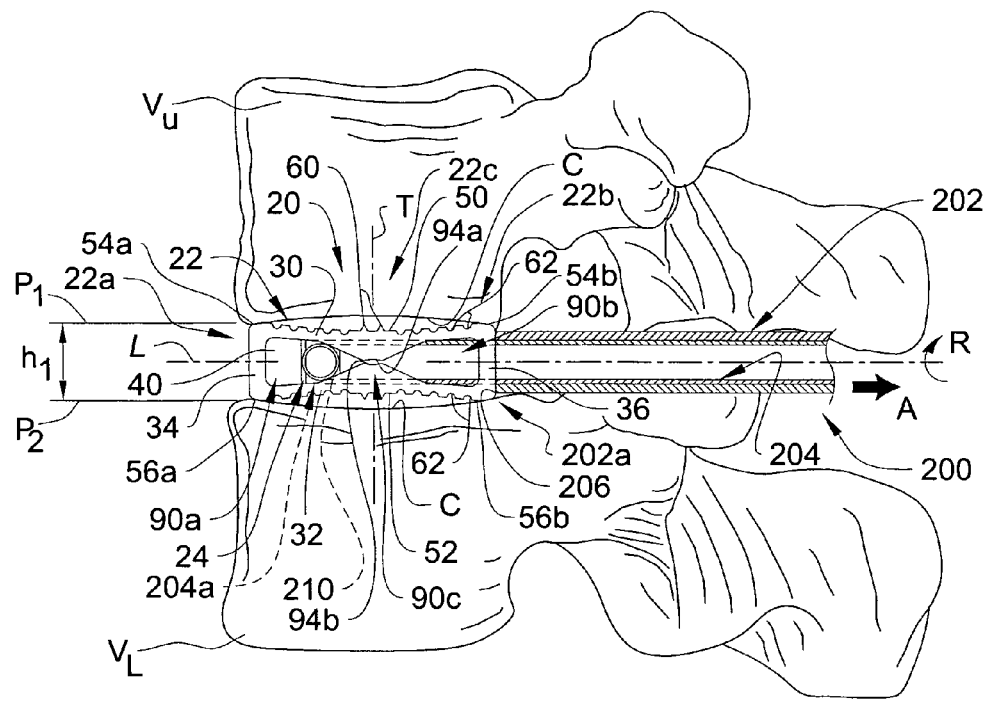
FIG. 7 is a side elevational view of the expandable intervertebral implant illustrated in FIG. 1, as shown in an initial, non-expanded state within an intervertebral disc space.
Figure 8:
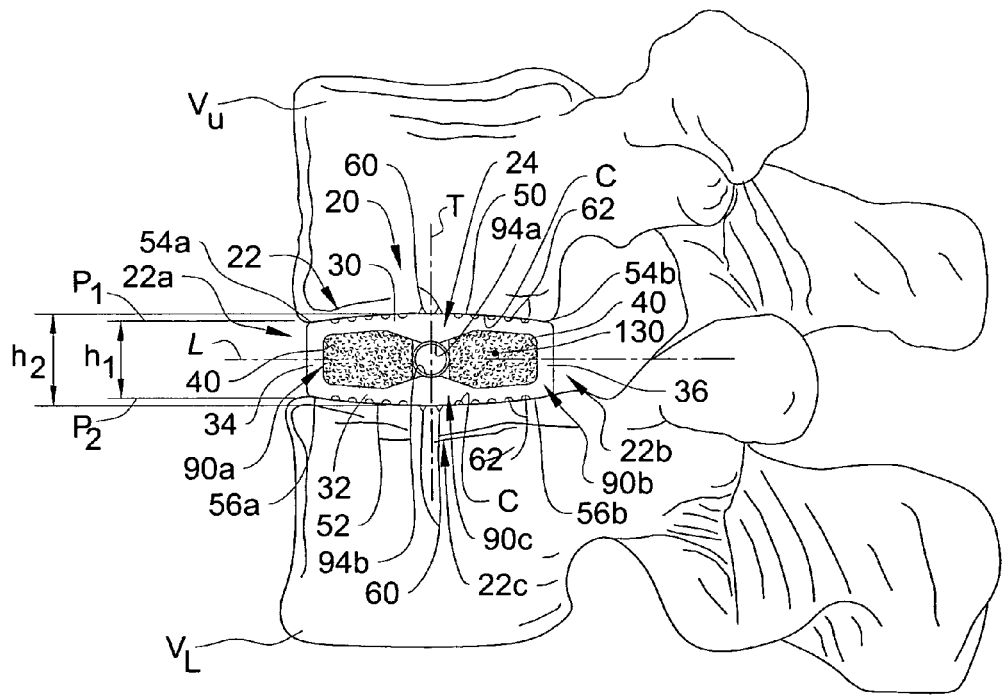
FIG. 8 is a side elevational view of the expandable intervertebral implant illustrated in FIG. 1, as shown in a fully expanded state within the intervertebral disc space.

Referring to FIG. 1, shown therein is an expandable intervertebral implant 20 according to one form of the present invention. The intervertebral implant 20 extends along a longitudinal axis L and is generally comprised of an expandable implant body 22 and an expansion member 24. As will be discussed in greater detail below, the expansion member 24 serves to transition the implant body 22 from an initial non-expanded state (as shown in FIG. 7) to an expanded state (as shown in FIG. 8) wherein expansion of the implant body 22 occurs generally along a transverse axis T. The expansion member 24 may also allow the implant body 22 to be retracted from the expanded state back toward the initial, non-expanded state. Further details regarding the features and operation of the expandable intervertebral implant 20 will be set forth below.

The components of the expandable intervertebral implant 20 are formed of a bio-compatible material. In one embodiment of the invention, the components of the intervertebral implant 20 are formed of a metallic material such as, for example, stainless steel and stainless steel alloys, titanium and titanium alloys, shape-memory alloys, cobalt chrome alloys, or any other suitable metallic material. In another embodiment of the invention, the components of the intervertebral implant 20 are formed of a non-metallic material such as, for example, a polymeric material, a ceramic material, a reinforced composite material, bone, a bone substitute material, or any other suitable non-metallic material.

Referring collectively to FIGS. 1-4, shown therein are further details regarding the expandable implant body 22. In the illustrated embodiment of the invention, the implant body 22 is configured as an expandable fusion cage including features that facilitate or promote bone growth into and/or through the implant 20 to achieve arthrodesis between the adjacent vertebral bodies, the details of which will be discussed below. However, it should be understood that in other embodiments of the invention, the implant body 22 may be configured as an expandable spacer or plug.

In one embodiment of the invention, the expandable implant body 22 comprises of upper and lower axial walls 30, 32 extending generally along the longitudinal axis L and spaced apart along transverse axis T, and a pair of end walls 34, 36 extending transversely between and interconnecting opposing end portions of the upper and lower walls 30, 32. The upper and lower axial walls 30, 32 and the transverse end walls 34, 36 cooperate to define an inner chamber 40 extending generally along the longitudinal axis L. In the illustrated embodiment of the implant body 22, the axial walls 30, 32 and the transverse walls 34, 36 provide the implant body 22 with a generally rectangular axial cross-section. However, it should be understood that other shapes and configurations of the implant body 22 are also contemplated as falling within the scope of the present invention.

Figures 2, 4:
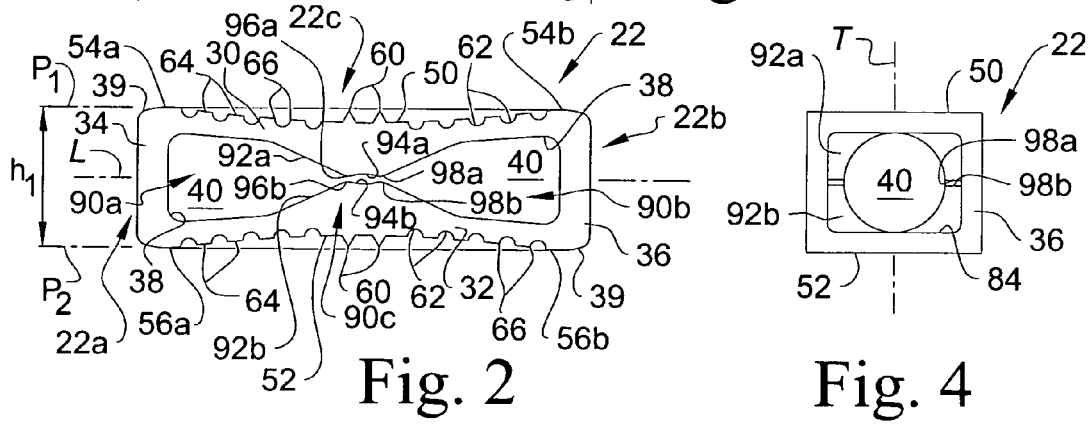
FIG. 2 is a side elevational view of an expandable implant body according to one embodiment of the present invention for use in association with the expandable intervertebral implant illustrated in FIG. 1.
FIG. 4 is an end elevational view of the expandable implant body illustrated in FIG. 2.

In one aspect of the invention, the upper and lower walls 30, 32 are coupled to the end walls 34, 36 in a manner that allows the upper and lower walls 30, 32 to be outwardly displaced relative to one another via the expansion member 24. In another aspect of the invention, the expansion member 24 co-acts with the upper and lower walls 30, 32 to flexibly deform the upper and lower walls 30, 32 in an outward direction relative to one another to provide for outward expansion of the implant body 22 generally along the transverse axis T from the non-expanded state illustrated in FIG. 7 to the expanded state illustrated in FIG. 8. Such outward deformation is primarily attributable to the flexible nature of the upper and lower walls 30, 32 and/or the flexible interconnection between the upper and lower walls 30, 32 and the end walls 34, 36. In one embodiment of the invention, the upper and lower walls 30, 32 are formed integral with the end walls 34, 36 to define a unitary, single-piece implant body 22. However, it is also contemplated that the upper and lower walls 30, 32 and the end walls 34, 36 may be formed separately and connected together to form a multi-piece expandable body assembly. As shown in FIG. 2, in a further embodiment, the points of connection between the upper and lower walls 30, 32 and the end walls 34, 36 include rounded inner surfaces 38 to provide increased flexibility to facilitate outward deformation of the upper and lower walls 30, 32 during expansion of the implant body 22. Additionally, the points of connection between the upper and lower walls 30, 32 and the end walls 34, 36 include rounded outer surfaces 39 to provide rounded proximal and distal ends which aid in the insertion of the implant body 22 between adjacent vertebral bodies and into the disc space, and also facilitate the possible removal of the implant body 22 from the intervertebral disc space.

In a further aspect of the invention, when in the non-expanded state (FIG. 7), the outer surfaces of the upper and lower walls 30, 32 define a recessed region extending inwardly along the transverse axis T. In the illustrated embodiment, the recessed region defined by the upper and lower walls 30, 32 comprises an inwardly extending concave curvature. However, other types and configurations of recessed regions are also contemplated as falling within the scope of the present invention. As will be discussed in greater detail below, the recessed region or concave curvature provides the intervertebral implant 20 with a lower overall vertical profile to facilitate insertion of the implant 20 into the disc space without having to distract the adjacent vertebrae apart to accommodate for the additional height that would otherwise be presented by teeth or other surface projections extending from the upper and lower walls 30, 32. However, as shown in FIG. 8, once the intervertebral implant 20 is inserted into the disc space, expansion of the implant body 22 causes outward deformation of the upper and lower walls 30, 32 wherein the recessed region or concave curvature is outwardly expanded generally along the transverse axis T. In the illustrated embodiment, expansion of the implant body 22 provides each of the upper and lower walls 30, 32 with an outwardly extending convex curvature relative to the longitudinal axis L. As will be discussed below, the convex curvature defined by each of the upper and lower walls 30, 32 when the implant 20 is transitioned to the expanded state corresponds to a concave surface curvature defined by each of the adjacent vertebral bodies.

The upper and lower walls 30, 32 of the implant body 22 define upper and lower engagement surfaces 50, 52. In one embodiment of the invention, the upper and lower engagement surfaces 50, 52 in turn define upper bearing surfaces 54a, 54b and lower bearing surfaces 56a, 56b adjacent the end walls 34, 36. As will be discussed below, the upper and lower bearing surfaces 54a, 54b and 56a, 56b contact and bear against the cortical rim/apophyseal ring region of the respective upper and lower vertebral bodies $V_U$, $V_L$ (FIGS. 7-9) to provide support and resistance to a substantial amount of the compressive forces exerted onto the implant body 22. In the illustrated embodiment of the invention, the upper and lower bearing surfaces 54a, 54b and 56a, 56b are substantially smooth and devoid of any steps, protrusions, projections or irregularities. However, it should be understood that in other embodiments, the upper and lower bearing surfaces may define anchoring features to aid in engaging and gripping vertebral bone.

In a further embodiment of the invention, the upper and lower engagement surfaces 50, 52 of the implant body 22 include a number of anchor elements positioned axially between the upper and lower bearing surfaces 54a, 54b and 56a, 56b. The anchor elements are adapted for engagement with the adjacent vertebral bodies $V_U$, $V_L$ to prevent or inhibit movement of the implant body 22 and/or to facilitate bone growth onto the implant body 22 subsequent to implantation within the intervertebral disc space. In one embodiment, the anchor elements comprise a number of teeth or surface protrusions 60 projecting from the upper and lower engagement surfaces 50, 52. In another embodiment, the anchor elements comprise a number of grooves 62 cut into the upper and lower engagement surfaces 50, 52. However, it should be understood that other combinations and/or configurations of anchor elements are also contemplated for use in association with the implant body 22, including other features or elements extending from the upper and lower engagement surfaces 50, 52 such as, for example, spikes, threads, ridges, bumps, surface roughening, or any other element or feature suitable for anchoring to vertebral tissue. It should also be understood that in other embodiments of the invention, the upper and lower engagement surfaces 50, 52 of the implant body 22 need not necessarily include any anchor elements, but may alternatively define a substantially smooth configuration devoid of any surface projections or surface irregularities.

As shown in FIG. 2, the upper surfaces 54a, 54b adjacent the end walls 34, 36 are positioned along a first plane $P_1$, and the lower surfaces 56a, 56b adjacent the end walls 34, 36 are positioned along a second plane $P_2$. The distance between the first and second planes $P_1$, $P_2$ defines the maximum initial, non-expanded height $h_1$ of the implant body 22. As discussed above, when the implant body 22 is in the initial, non-expanded state, the outer surfaces of the upper and lower walls 30, 32 define an inwardly extending concave curvature. Due to this concave curvature, the teeth 60 (or other types of surface protrusions) projecting from the upper and lower engagement surfaces 50, 52 are at least partially positioned inward of the first and second planes $P_1$, $P_2$ which define the maximum non-expanded height $h_1$ of the implant body 22. In the illustrated embodiment of the invention, the teeth 60 are positioned entirely inward of the first and second planes $P_1$, $P_2$.

Since the teeth 60 preferably do not protrude or extend beyond the first and second planes $P_1$, $P_2$ when the implant body 22 is in the initial, non-expanded state, the teeth 60 do not interfere with the upper and lower vertebral bodies $V_U$, $V_L$ and potentially impede placement of the implant 20 during insertion into the disc space. Accordingly, distraction of the upper and lower vertebral bodies $V_U$, $V_L$ to accommodate for the height of the teeth 60 above the upper and lower surfaces of the walls 30, 32 is substantially avoided. Additionally, the implant body 22 may be provided with teeth 60 (or other types of surface projections) having a greater height than would otherwise be allowed for if the upper and lower walls 30, 32 did not define a concave curvature when in the initial, non-expanded state. Although the illustrated embodiment of the implant body 22 contemplates that the planes $P_1$ and $P_2$ are arranged substantially parallel to one another, it should be understood that in other embodiments of the invention, the planes $P_1$ and $P_2$ may be angled or tapered relative to one another. As should be appreciated, the implant body 22 may be configured such that the planes $P_1$ and $P_2$ are angled relative to one another to provide the implant body 22 with a tapered configuration that corresponds to the lordotic angle between the upper and lower vertebral bodies $V_U$, $V_L$.

In the illustrated embodiment of the implant body 22, the teeth 60 are arranged in rows extending laterally across a central portion 22c of the implant body 22. Although the implant body 22 is shown as having two rows of teeth 60 extending from the upper and lower engagement surfaces 50, 52, it should be understood that the inclusion of a single row of teeth or three or more rows of teeth are also contemplated. Additionally, it should be understood that the teeth 60 may be orientated in other directions such as, for example, in a direction parallel with the longitudinal axis L or arranged at an oblique angle relative to the longitudinal axis L. It should also be understood that one or more rows of teeth 60 may extend from other portions of the upper and lower engagement surfaces 50, 52, including the end portions 22a, 22b of the implant body 22. In one embodiment, the teeth 60 have a triangular-shaped configuration; however, other shapes and configurations of teeth are also contemplated as falling within the scope of the present invention. As shown in FIG. 8, upon transitioning of the implant body 22 to an expanded configuration, the teeth 60 are engaged/impacted into the vertebral endplates of the adjacent vertebral bodies $V_U$, $V_L$ to prevent or inhibit movement of the implant body 22 and possible expulsion from the disc space.

In the illustrated embodiment of the implant body 22, the grooves 62 are arranged in rows extending laterally across the end portions 22a, 22b of the implant body 22. Although the implant body 22 is shown as having ten grooves 60 formed into each of the upper and lower engagement surfaces 50, 52, it should be understood that any number of grooves 60 may be included. Additionally, it should be understood that the grooves 62 may be orientated in other directions such as, for example, in a direction parallel with the longitudinal axis L or arranged at an oblique angle relative to the longitudinal axis L. It should also be understood that grooves may be cut into other portions of the implant body 22, including the central portion 22c.

In one embodiment of the invention, the grooves 62 are formed by cutting swales or channels into the upper and lower engagement surfaces 50, 52 which are spaced apart so as to define lands or plateaus 64 that are substantially co-planar with the upper and lower engagement surfaces 50, 52. Edges or corners 66 are defined at the point where the grooves 62 and the lands 64 meet. In one embodiment, the grooves 62 are configured to have a groove width and a groove depth that is greater than the width of the lands 64. However, other configurations of the grooves 62 are also contemplated. Additionally, in the illustrated embodiment, the grooves 62 have a substantially circular configuration defining a substantially uniform radius or curvature. However, other shapes and configurations of the grooves 62 are also contemplated such as, for example, arcuate or bow-shaped grooves, V-shaped or U-shaped grooves, or any other suitable groove shape or configuration. As illustrated in FIG. 8, upon transitioning of the implant body 22 to an expanded configuration, the lands 64 engage the vertebral endplates of the adjacent vertebral bodies $V_U$, $V_L$ so as to position the grooves 62 in close proximity thereto to receive bone tissue therein and/or to facilitate bone growth onto the implant body 22. Additionally, the edges 66 formed between the grooves 62 and the lands 64 aid in preventing or otherwise inhibiting movement of the implant body 22 and possible expulsion from the disc space.

Figure 3:
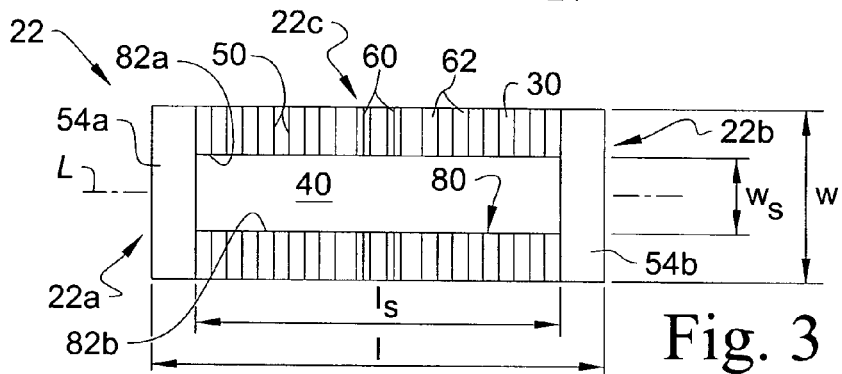
FIG. 3 is a top plan view of the expandable implant body illustrated in FIG. 2.

As shown most clearly in FIGS. 1 and 3, in one embodiment of the invention, the implant body 22 defines a bone in-growth opening or slot 80 extending transversely therethrough in communication with the inner chamber 40 and opening onto the upper and lower engagement surfaces 50, 52 of the walls 30, 32. In the illustrated embodiment, the slot 80 extends along substantially the entire length l of the implant body 22 and defines a pair of longitudinally extending and oppositely facing side surfaces 82a, 82b where the slot 80 extends through the upper and lower walls 30, 32. As should be appreciated, the bone in-growth slot 80 permits bone growth from the adjacent vertebral bodies and into and potentially through the implant body 22. Additionally, the slot 80 is also sized to receive a portion of the expansion member 24 therein, between the opposing side surfaces 82a, 82b, to aid in guiding the expansion member 24 generally along the longitudinal axis L to substantially prevent side-to-side displacement as the expansion member 24 is axially displaced through the implant body 22 during expansion of the intervertebral implant 20.

Although the implant body 22 is illustrated as having a single bone in-growth slot 80 extending transversely through and along substantially the entire length l of the implant body 22, it should be understood that the implant body 22 may be configured to have any number of bone in-growth slots, including two or more bone in-growth slots or openings positioned at various locations along the length of the implant body 22. Additionally, although the bone in-growth slot 80 is illustrated as having a generally rectangular configuration having a slot length $l_s$ extending along substantially the entire length l of the implant body 22, and a slot width $w_s$ extending across about one-third of the width w of the implant body 22, it should be understood that other shapes, configurations and sizes of bone in-growth openings are also contemplated. It should further be understood that although the bone in-growth slot 80 is illustrated and described as communicating with the inner chamber 40, in other embodiments, the slot 80 need not necessarily extend entirely through the upper and lower walls 30, 32.

As shown most clearly in FIGS. 1 and 4, in the illustrated embodiment of the implant body 22, an axial opening 84 extends through each of the end walls 34, 36 in communication with the inner chamber 40. As will be discussed in further detail below, the axial openings 84 are sized to receive an end portion of an instrument therein for engagement with the expansion member 24 to facilitate transitioning of the implant body 22 to an expanded configuration. Additionally, the axial openings 84 also permit bone growth from the adjacent vertebral bodies into the inner chamber 40 of the implant body 22 from posterior and anterior directions. In the illustrated embodiment of the invention, the axial openings 84 have a generally rectangular configuration and have a relatively large size which encompasses almost all of the end walls 34, 36. However, it should be understood that other sizes, shapes and configurations of the axial openings 84 are also contemplated as falling within the scope of the present invention. It should also be understood that in other embodiments of the invention, only one of the end walls 34, 36 defines an axial opening 84, with the other end wall having a substantially solid configuration to close off the end of the implant body 22 opposite the axial opening 84.

As illustrated in FIGS. 1 and 2, in one embodiment of the invention, the inner chamber 40 includes a number of distinct compartments or sections positioned along the length l of the implant body 22. In the illustrated embodiment of the implant body 22, the inner chamber 40 includes end compartments 90a and 90b positioned adjacent the end portions 22a and 22b of the implant body 22, and an intermediate or center compartment 90c positioned adjacent the central portion 22c of the implant body 22. However, it should be understood that the inner chamber 40 may include any number of compartments, including a single compartment, two compartments, or four or more compartments. In the illustrated embodiment of the invention, each of the chamber compartments 90a, 90b, 90c extends laterally through the entire width w of the implant body 22, thereby providing increased flexibility for expansion of the implant body 22 and also providing the implant body 22 with open sides to permit bone growth into the inner chamber 40 from lateral directions.

In the illustrated embodiment of the implant body 22, the end compartments 90a, 90b each have a tapered region wherein the inner surfaces of the upper and lower walls 30, 32 adjacent the intermediate compartment 90c taper inwardly toward one another to define a pair of opposing ramped surfaces 92a, 92b. The center compartments 90c has an arcuate configuration, with the inner surfaces of the upper and lower walls 30, 32 defining a pair of opposing concave surfaces 94a, 94b having substantially the same curvature as the upper and lower arcuate engagement surfaces 120a, 120b defined by the expansion member 24 (FIGS. 5 and 6), the details of which will be discussed below. The point of intersection between the ramped surfaces 92a, 92b of the end compartments 90a, 90b and the concave surfaces 94a, 94b of the center compartment 90c defines opposing apices or vertices 96a, 96b and 98a, 98b positioned on either side of the center compartment 90c. Although the illustrated embodiment of the implant body 22 depicts the inner chamber 40 and the compartments 90a, 90b and 90c as having a particular shape and configuration, it should be understood that other suitable shapes and configurations are also contemplate as falling within the scope of the present invention. In one embodiment of the invention, the end compartments 90a, 90b are substantially symmetrical to one another relative to the transverse axis T, the purpose of which will be discussed below.

Figure 5:
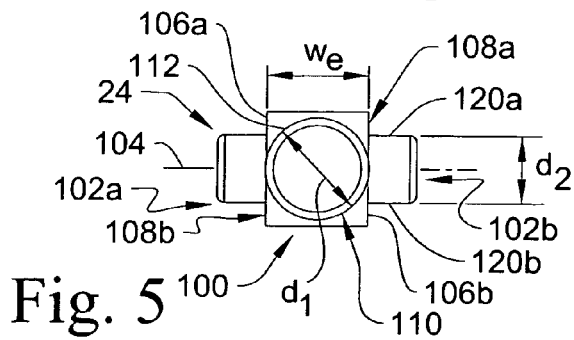
FIG. 5 is an end elevational view of an expansion member according to one embodiment of the present invention for use in association with the expandable intervertebral implant illustrated in FIG. 1.
Figure 6:
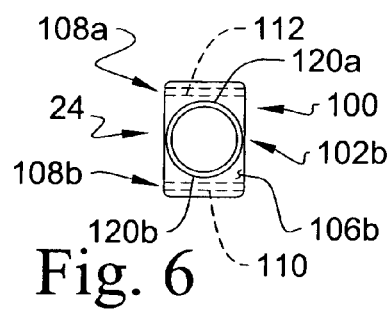
FIG. 6 is a side elevational view of the expansion member illustrated in FIG. 5.

Referring to FIGS. 5 and 6, shown therein is the expansion member 24 according to one embodiment of the present invention. In the illustrated embodiment, the expansion member 24 includes a central main body portion 100 and a pair of side portions 102a, 102b projecting laterally from the central portion 100 and arranged generally along a lateral axis 104.

In one embodiment of the invention, the central portion 100 of the expansion member 24 has a generally rectangular or square cross section that defines substantially flat or planar side surfaces 106a, 106b from which the side portions 102a, 102b extend. However, it should be understood that other shapes and cross sections of the central portion 100 are also contemplated such as, for example, hexagonal or polygonal cross sections, or circular or elliptical cross sections, with the side surfaces 106a, 106b having a curved or arcuate configuration, or any other shape or configuration that would occur to one of skill in the art. At least the upper and lower segments 108a, 108b of the central portion 100 define a width $w_e$ between the side surfaces 106a, 106b that closely corresponds to the width $w_s$ of the slot 80 extending through the implant body 22. As will be discussed below, the upper and lower segments 108a, 108b of the central portion 100 are displaced through the slot 80 and along the opposing side surfaces 82a, 82b as the expansion member 24 is axially displaced through the inner chamber 40 during transitioning of the implant body 22 toward the expanded configuration illustrated in FIG. 8.

In the illustrated embodiment, the central portion 100 defines a passage 110 having a diameter $d_1$. The passage 110 extends entirely through the central portion 100 and is arranged generally along the longitudinal axis L when the expansion member 24 is positioned within the implant body 22. The passage 110 is sized to receive a distal end portion of a surgical instrument 200 (FIG. 7) which is configured to axially displace the expansion member 24 through the inner chamber 40 during transitioning of the implant body 22 to an expanded configuration, the details of which will be discussed below. In one embodiment, the passage 110 has a generally circular cross section and includes internal threads 112 that define a continuous thread pattern through the axial passage 110 which are adapted for engagement with a threaded distal end portion of the surgical instrument 200. However, it should be understood that other shapes and configurations of the axial passage 110 are also contemplated for use in association with the present invention.

In a further embodiment of the invention, the side portions 102a, 102b of the expansion member 24 each have a generally circular cross section relative to the lateral axis 104 and define an outer diameter $d_2$. As shown in FIG. 5, the diameter $d_2$ of the axial passage 110 extending through the central portion 100 of the expansion member 24 is greater than the outer diameter $d_2$ of the side portions 102a, 102b. As should be appreciated, absent the enlarged central portion 100, the maximum diameter $d_1$ of the axial passage 110 extending through the expansion member 24 would be somewhat less than the outer diameter $d_2$ of the side portions 102a, 102b. As will be discussed below, providing the passage 110 with a relatively large diameter $d_1$ facilitates the passage of graft material (or other types of material) through the expansion member 24 and into one of the end compartments 90a, 90b defined by the inner chamber 40 of the implant body 22. Additionally, providing the passage 110 with a relatively large diameter $d_1$ also provides more stable and secure engagement with the distal end portion of the surgical instrument 200.

In the illustrated embodiment, each of the side portions 102a, 102b of the expansion member 24 has a generally circular cross section which defines upper and lower engagement surfaces 120a, 120b having a curved or arcuate configuration. However, it should be understood that other shapes and cross sections of the side portions 102a, 102b and the upper and lower engagement surfaces 120a, 120b are also contemplated. For example, in other embodiments of the invention, the side portions 102a, 102b may have triangular, rectangular, hexagonal or polygonal cross sections with the upper and lower engagement surfaces 120a, 120b having angled or substantially flat or planar configurations, or any other shape or configuration that would occur to one of skill in the art. The side portions 102a, 102b provide the expansion member 24 with an overall width that is less than or equal to the overall width of the implant body 22 so that the side portions 102a, 102 do not extend laterally beyond the side surfaces of the implant body 22. As will be discussed in greater detail below, the upper and lower engagement surfaces 120a, 120b of the side portions 102a, 102b slide along the ramped surfaces 92a, 92b of the upper and lower walls 30, 32 as the expansion member 24 is axially displaced through the inner chamber 40 during transitioning of the implant body 22 to the expanded configuration illustrated in FIG. 8.

Referring now to FIG. 7, shown therein is the intervertebral implant 20 positioned within the disc space between the upper and lower vertebral bodies $V_U$, $V_L$ in an initial, non-expanded configuration. As discussed above, the maximum initial height $h_1$ of the implant body 22 when in the initial, non-expanded state is the distance between the upper and lower end surfaces 54a, 56a and 54b, 56b adjacent the end walls 34, 36, respectively, which in the illustrated embodiment is the distance between the first and second planes $P_1$, $P_2$. In order to minimize distraction of the upper and lower vertebral bodies $V_U$, $V_L$ and avoid over distraction of the disc space, the initial height $h_1$ of the implant body 22 is preferably selected to correspond to the natural disc space height. In one embodiment, the initial height $h_1$ of the implant body 22 closely corresponds to the natural disc space height adjacent the cortical rim/apophyseal ring region adjacent the anterior/posterior portions of the upper and lower vertebral bodies $V_U$, $V_L$. However, other initial heights $h_1$ of the implant body 22 are also contemplated as falling within the scope of the present invention. As also discussed above, due to the inwardly extending configuration of the upper and lower walls 30, 32, the teeth 60 (or other types of surface projections) extending from the upper and lower walls 30, 32 do not protrude or extend beyond the first and second planes $P_1$, $P_2$, thereby avoiding interference between the teeth 60 and the upper and lower vertebral bodies $V_U$, $V_L$ which could otherwise impede insertion of the implant 20 into the intervertebral disc space.

A surgical instrument 200 according to one embodiment of the invention is engaged to the intervertebral implant 20 to aid in the insertion of the implant 20 into the disc space and to transition the implant body 22 to the expanded configuration illustrated in FIG. 8. In one embodiment, the surgical instrument 200 generally includes an outer sleeve 202 engagable with the implant body 22, and an inner drive shaft 204 positioned within the outer sleeve 202 and engagable with the expansion member 24. Although a specific configuration of the surgical instrument 200 has been illustrated and described herein, it should be understood that other suitable types and configurations of surgical instruments are also contemplated for use in association with the present invention, and that the elements and operation thereof may differ from the embodiment of the surgical instrument 200 illustrated and described herein. For example, another type of instrument suitable for use in association with the present invention is illustrated and described in U.S. Pat. No. 6,436,140 to Liu et al., the entire contents of which are hereby incorporated herein by reference.

The surgical instrument 200 may include a first handle (not shown) attached to the outer sleeve 202 to aid in the manipulation and handling of the intervertebral implant 20, and a second handle (not shown) attached to the inner drive shaft 204 to aid in actuation of the drive shaft 204 to expand the implant 20. In one embodiment, the handle associated with the outer sleeve 202 may be configured as a counter torque-type handle that is easily grasped by the surgeon during manipulation and handling of the implant 20 (e.g., during insertion of the implant 20 into the disc space), and which may also be used to oppose any torque forces that may be exerted onto the outer sleeve 202 during actuation or expansion of the implant 20 (e.g., during displacement of the expansion member 24 through the inner chamber 40 of the implant body 22). In another embodiment, the handle associated with the inner drive shaft 204 may be configured as a T-handle that is manipulated by the surgeon to impart a rotational force onto the drive shaft 204, which in turn displaces the expansion member 24 through the inner chamber 40 of the implant body 22 to expand the implant 20 subsequent to insertion into the disc space. However, it should be understood that other suitable types and configurations of handles are also contemplated for use in association with the instrument 200, and that the elements and operation thereof may differ from the embodiment of the surgical instrument 200 illustrated and described herein.

The outer sleeve 202 of the surgical instrument 200 has a distal end portion 202a adapted for engagement with the implant body 22. In one embodiment of the invention, the distal end portion 202a defines an engagement surfaces 206 formed by the distal end of the sleeve 202, or by a shoulder or boss that can be abutted or compressed against either of the end walls 34, 36 of the implant body 22, the purpose of which will be discussed below. In another embodiment, the instrument 200 and the implant body 22 may include features that cooperate with one another to prevent rotation of the implant body 22 relative to the outer sleeve 202. In a specific embodiment, one or more projections associated with the distal end portion 202a of the outer sleeve 202 may be inserted into a recessed area formed in either of the end walls 34, 36 of the implant body 22. For example, one or more pins associated with the distal end portion 202a may be inserted into openings or recesses formed in the end walls 34, 36 of the implant body 22. In another specific embodiment, the distal-most end portion of the instrument 200 may be provided with an outer profile that closely corresponds to the inner profile of the axial opening 84 formed through the end walls 34, 36 of the implant body 22. In yet another specific embodiment, the instrument 200 may include a pair of prongs (not shown) extending axially from the distal end portion 202a of the sleeve 202 and including transverse flanges extending inwardly toward one another in an opposing manner. As should be appreciated, positioning of the transverse flanges into either of the end compartment 90a, 90b of the implant body 22 would function to secure the outer sleeve 202 to the implant body 22 and to prevent rotation of the implant body 22 relative to the outer sleeve 202. It should be understood that other types of engagement features between the sleeve 202 and the implant body 22 are also contemplated as would occur to one of skill in the art including, for example, threaded engagement, clamping engagement, keyed engagement, tongue-and-groove engagement, frictional engagement, or any other suitable means for engagement.

The inner drive shaft 204 of the surgical instrument 200 is positioned within the outer sleeve 202 in a manner which allows rotation of the drive shaft 204 within the sleeve 202 while constraining axial displacement of the drive shaft 204 through the sleeve 202. The drive shaft 204 includes a distal end portion 204a that extends through the axial opening 84 in the end wall 36 of the implant body 22 and into engagement with the expansion member 24. In one embodiment, at least the distal end portion 204a of the drive shaft 204 includes external threads 210 adapted for threading engagement with the internal threads 112 formed along the passage 110 in the central portion 100 of the expansion member 24 to thereby engage the drive shaft 204 to the expansion member 24. However, it should be understood that other types of engagement between the drive shaft 204 and the implant body 22 are also contemplated, such as, for example, abutting engagement, clamping engagement, keyed engagement, tongue-and-groove engagement, frictional engagement, or any other suitable means for engagement.

As shown in FIG. 7, in one embodiment of the invention, the expansion member 24 is initially positioned in the end compartment 90a adjacent the distal end 22a of the implant body 22 and, as will be discussed below, expansion of the implant 20 is accomplished by pulling the expansion member 24 toward the proximal end 22b of the implant body 22 until the expansion member 24 is positioned within the center compartment 90c. In another embodiment of the invention, the expansion member 24 may be initially positioned in the end compartment 90b adjacent the proximal end 22b of the implant body 22, with expansion of the implant 20 resulting from pushing the expansion member 24 toward the distal end 22a until the expansion member 24 is positioned within the center compartment 90c. However, the initial positioning the expansion member 24 in the distal end compartment 90a and pulling the expansion member 24 into the center compartment 90c results in the relatively simpler overall design of a "pull" style instrument, such as the surgical instrument 200 illustrated and described herein. For example, with regard to the pull-style instrument 200, engagement between the outer sleeve 202 and the implant body 22 can be accomplished via non-positive, abutting engagement since pulling of the expansion member 24 toward the proximal end 22b of the implant body 22 compresses the proximal end wall 36 against the distal end portion of the outer sleeve 204. Accordingly, positive locking engagement between the outer sleeve 202 and the implant body 22 is not required, as would be the case with a "push" style instrument. Additionally, a pull-style instrument also tends to provide a greater degree of control over the forces required to expand the implant 20 compared to that of a push-style instrument.

As shown in FIG. 7, the distal end portion 202a of the outer sleeve 202 is engaged against the proximal end wall 36, with the threaded distal portion 204a of the inner drive shaft 204 extending through the axial opening 84 in the end wall 36 and into threading engagement with the threaded passage 110 in the central portion 100 of the expansion member 24. As should be appreciated, since the drive shaft 204 is axially constrained relative to the outer sleeve 202 (and hence relative to the implant body 22), rotation of the drive shaft 204 in a direction of rotation R will threadingly engage the distal end portion 204a of the drive shaft 204 along the threaded passage 110, which will in turn result in the expansion member 24 being drawn in the direction of arrow A toward the center compartment 90c of the implant body 22.

Although a specific instrument and technique for displacing the expansion member 24 relative to the implant body 22 has been illustrated and described herein, it should be understood that other instruments and techniques are also contemplated as falling within the scope of the present invention. For example, the drive shaft 204 may be axially displaced relative to the outer sleeve 202 via threading engagement between the drive shaft 204 and the outer sleeve 202, as illustrated, for example, in U.S. Pat. No. 6,436,140 to Liu et al. In this manner, rotation of the drive shaft 204 would result in axial displacement of the drive shaft 204, which would in turn result in axial displacement of the expansion member 24 relative to the implant body 22. In other embodiments, the drive shaft 204 may simply be pulled in the direction of arrow A, which would in turn result in axial displacement of the expansion member 24 toward the center compartment 90c of the implant body 22. Additionally, although the illustrated embodiment of the invention contemplates the use of linear displacement of the expansion member 24 relative to the implant body 22 to expand the implant 20, it should be understood that in other embodiments of the invention, the implant body 22 and the expansion member 24 may be configured such that transverse, rotational and/or pivotal displacement of the expansion member 24 relative to implant body 22 serves to expand the implant body 22 along the transverse axis T. For example, in an alternative embodiment of the invention, the expansion member 24 may be configured to have an oblong or cam-like configuration such that rotation of the expansion member 24 within the center compartment 90c results in expansion of the implant body 22.

As should be appreciated, axial displacement of the expansion member 24 in the direction of arrow A will correspondingly transition the implant body 22 toward the fully expanded configuration shown in FIG. 8. More specifically, axial displacement of the expansion member 24 from the distal end compartment 90a toward the center compartment 90c slidably engages the upper and lower engagement surface 120a, 120b defined by the side portions 102a, 102b of the expansion member 24 along the opposing ramped surfaces 92a, 92b defined by the implant body 22. As a result, the upper and lower walls 30, 32 of the implant body 22 are driven away from one another and are outwardly deformed along the transverse axis T to transition the implant body 22 from the initial, non-expanded configuration illustrated in FIG. 7 toward the expanded configuration illustrated in FIG. 8. The expansion member 24 is further displaced in an axial direction until positioned within the center compartment 90c of the inner chamber 40, with the side portions 102a, 102b of the expansion member 24 positioned within the recessed areas formed by the opposing concave surfaces 94a, 94b and captured between the opposing apices/vertices 96a, 96b and 98a, 98b.

It should be appreciated that positioning of the side portions 102a, 102b of the expansion member 24 within the opposing concave surfaces 94a, 94b and between the opposing apices/vertices 96a, 96b and 98a, 98b retains the expansion member 24 within the center compartment 90c and resists or inhibits further axial displacement of the expansion member 24 to thereby maintain the implant body 22 in the expanded configuration shown in FIG. 8, even after the drive shaft 204 is detached from the expansion member 24. It should also be appreciated that during expansion of the implant body 22, once the expansion member 24 is positioned beyond the pair of opposing apices/vertices 96a, 96b and enters or "clicks" into the center compartment 90c, the amount of linear driving force or rotational torque exerted onto the drive shaft 204 of the instrument 200 will significantly and abruptly decrease. This abrupt drop-off in driving force or torque provides the surgeon with a perceptible indication that the expansion member 24 is properly positioned within the center compartment 90c and that the desired amount of expansion has been attained.

Additionally, as indicated above, the upper and lower segments 108a, 108b of the expansion member 24 define a width $w_e$ between the side surfaces 106a, 106b (FIG. 5) that closely corresponds to the width $w_s$ of the slot 80 extending through the implant body 22 (FIG. 3). Accordingly, as the expansion member 24 is displaced through the inner chamber 40 of the implant body 22 to transition the implant body 22 toward an expanded configuration, the upper and lower segments 108a, 108b of the central portion 100 are displaced through the slot 80, with the side surfaces 106a, 106b being displaced along the opposing side surfaces 82a, 82b of the slot 80. Displacement of the upper and lower segments 108a, 108b of the central portion 100 through the slot 80 aids in guiding the expansion member 24 through the inner chamber 40 during expansion of the implant body 22. Additionally, the relatively close fit between the side surfaces 106a, 106b of the expansion member 24 and the opposing side surfaces 82a, 82b of the slot 80 provides additional support and rigidity to the implant body 22, and particularly resists side-to-side or lateral forces exerted onto the implant 20 by the upper and lower vertebral bodies $V_U$, $V_L$.

As shown in FIG. 8, expansion of the implant body 22 increases the overall height of the implant body 22 adjacent the central portion of the implant to an expanded height $h_2$ that is substantial equal to the height adjacent the central portion of the disc space. As should be appreciated, the difference between the initial height $h_1$ and the expanded height $h_2$ of the implant body 22 corresponds to the difference between the diameter $d_1$ (or height) of the side portions 102a, 102b of the expansion member 24 (FIGS. 5 and 6) and the non-expanded distance $d_2$ between the concave surfaces 94a, 94b of the center compartment 90c of the implant body 22 (FIG. 2). Accordingly, expansion of the implant body 22 can be easily and accurately controlled by providing the expansion member 24 with side portions 102a, 102b having a select diameter $d_1$ (or height) and/or by providing the center compartment 90c with a configuration having a select non-expanded distance $d_2$ between the concave surfaces 94a, 94b.

When the implant body 22 is transitioned to the expanded configuration, the upper and lower walls 30, 32 are outwardly deformed away from one another along the transverse axis T to increase the overall height $h_2$ of the implant body 22. Since the end portions of the upper and lower walls 30, 32 are integrally connected to the end walls 34, 36, the end portions of the upper and lower walls 30, 32 remain relatively stationary and expansion of the implant body 22 adjacent the end portions 22a, 22b is limited. However, since the central portions of the upper and lower walls 30, 32 are not interconnected, expansion of the implant body 22 occurs primarily along the central portion of the implant body 22. As a result, upon expansion of the implant body 22, the upper and lower walls 30, 32 each form an outwardly extending convex curvature relative to the longitudinal axis L. The convex curvature of the outwardly deformed upper and lower walls 30, 32 preferably substantially corresponds to the anterior-to-posterior surface curvature C defined by the vertebral endplates of the adjacent vertebral bodies $V_U$, $V_L$. Additionally, expansion of the implant body 22 generally along the transverse axis T imbeds or impacts the teeth 60 extending from the upper and lower engagement surfaces 50, 52 into the vertebral endplates to resist migration and possible expulsion of the implant body 22 from the disc space. Following expansion of the implant body 22, the surgical instrument 200 is disengaged from the expansion member 24 and removed from the patient. In the illustrated embodiment, this may be accomplished by simply rotating the drive shaft in a direction opposite the initial direction of rotation R until the threaded distal end portion 204a is disengaged from the threaded passage 110.

If removal of the expanded implant 20 from the disc space is required due to non-optimal placement of the implant 20 or for other reasons, due to the symmetrical nature of the end compartments 90a, 90b, the implant body 22 can be transitioned from the expanded configuration (FIG. 8) back toward the initial, non-expanded configuration (FIG. 7) by simply repositioning the expansion member 24 from the center compartment 90c to the proximal end compartment 90b. As should be appreciated, further axial displacement of the expansion member 24 is accomplished by rotating the drive shaft 204 in a direction of rotation R, which will in turn draw the expansion member 24 in the direction of arrow A until the side portions 102a, 102b of the expansion member 24 are removed from the concave surfaces 94a, 94b of the center compartment 90c and positioned within the proximal end compartment 90b of the implant body 22. Such repositioning will in turn cause the flexible implant body 22 to retract toward the initial, non-expanded configuration illustrated in FIG. 7 wherein the teeth 60 will once again be inwardly recessed relative to the planes $P_1$, $P_2$ so as to avoid interfering with the upper and lower vertebral bodies $V_U$, $V_L$ which may otherwise impede removal of the implant 20 from the disc space. The implant 20 may then be removed from the disc space and reintroduced therein using the insertion and expansion procedures outlined above to reposition the implant 20 into a revised position within the disc space.

In a further aspect of the invention, following the insertion and expansion of the implant 20 within the disc space, a bone growth promoting material 130 (FIGS. 8 and 9) is loaded into the inner chamber 40 of the implant body 22 to facilitate or promote bone growth from the upper and lower vertebral bodies $V_U$, $V_L$, through the slot 80 extending through the upper and lower walls 30, 32, and into and possibly through the implant body 22. In one embodiment, the bone growth promoting material 130 comprises of a bone graft material, a bone morphogenic protein (BMP), or any other suitable bone growth promoting material or substance, including but not limited to bone chips or bone marrow, a demineralized bone matrix (DBM), mesenchymal stem cells, and/or a LIM mineralization protein (LMP). It should be understood that the bone growth promoting material 130 can be used with or without a suitable carrier.

In one embodiment of the invention, the bone growth promoting material 130 is loaded or packed into the inner chamber 40 via the axial opening 84 in the end wall 36 subsequent to insertion and expansion of the implant body 22. However, in an alternative embodiment, a portion of the bone growth promoting material 130 may be pre-loaded into the inner chamber 40 prior to insertion and expansion of the implant body 22. As indicated above, the size of the passage 110 in the central portion 100 of the expansion member 24 is relatively large. As a result, the bone growth promoting material 130 may be conveyed through the large passage 110 in the expansion member 24 and into the distal end compartment 90a of the inner chamber 40. Once the distal end compartment 90a is fully loaded, additional bone growth promoting material 130 may be loaded into the proximal end compartment 90b of the inner chamber 40. As should be appreciated, due to the inclusion of the relatively large passage 110 in the expansion member 24, the bone growth promoting material 130 need not be preloaded into the distal end compartment 90a prior to insertion and expansion of the implant 20 within the disc space. Additionally, conveying the bone growth promoting material 130 through the relatively large passage 110 in the expansion member 24 allows the entire inner chamber 40 to be tightly packed with the bone growth promoting material 130. Additionally, bone graft, morselized autograft bone or a similar type of material may be positioned laterally adjacent the expanded implant body 22 to further promote fusion with the adjacent vertebral bodies $V_U$, $V_L$.

Having illustrated and described the elements and operation of the intervertebral implant 20, reference will now be made to a technique for implanting the intervertebral implant 20 within a disc space according to one embodiment of the invention. However, it should be understood that other implantation techniques and procedures are also contemplated, and that the following technique in no way limits the scope of the present invention.

In one embodiment of the invention, access to the spinal column and insertion of the intervertebral implant 20 into the disc space is accomplished via a posterior surgical approach. However, it should be understood that access and insertion of the intervertebral implant 20 into the disc space may be accomplished via other surgical approaches such as, for example, an anterior approach or a lateral approach. In another embodiment of the invention, the intervertebral implant 20 is used to treat the lumbar region of the spine, with the upper and lower vertebral bodies $V_U$, $V_L$ comprising lumbar vertebral bodies. However, it should be understood that the present invention is also applicable to other portions of the spine such as, for example, the cervical, thoracic or sacral regions of the spinal column.

Initially, the portion of the spinal column to be treated is identified and accessed from a posterior approach using known surgical techniques. At least a portion of the natural intervertebral disc is removed via a total or partial discectomy to provide an opening for receiving the intervertebral implant 20 between the upper and lower vertebral bodies $V_U$, $V_L$. The disc space is then distracted to a height substantially equal to the natural disc space height. Prior to insertion of the intervertebral implant 20, the disc space and the endplates of the upper and lower vertebral bodies $V_U$ and $V_L$ may be prepared using various cutting tools and/or other types of surgical instruments (e.g., curettes, chisels, etc.). One example of a cutting instrument suitable for preparing the vertebral bodies $V_U$, $V_L$ is illustrated and described in U.S. Pat. No. 6,610,089 to Liu et al., the contents of which have been incorporated herein by reference. However, it should be understood that other types and configurations of cutting instruments are also contemplated for use in association with the present invention.

In one embodiment of the present invention, the cutting instrument used to prepare the vertebral bodies $V_U$, $V_L$ is adapted to cut and remove bone tissue from the vertebral endplates while substantially retaining the natural concave curvature of the endplates and avoiding cutting into the cortical rim/apophyseal ring region adjacent the anterior/posterior portions of the vertebral endplates. The cutting instrument may also be configured to collect bony debris or chips generated during the cutting operation for subsequent insertion into the inner chamber 40 of the implant body 22 to promote arthrodesis. As illustrated in FIGS. 7 and 8, each of the prepared vertebral endplates defines a recessed area or surface curvature C that is generally concave in an anterior-to-posterior direction. As should be appreciated, the recessed area or surface curvature C defined by the vertebral bodies $V_U$, $V_L$ receives the outwardly deformed upper and lower walls 30, 32 of the expanded implant body 22 so as to position the upper and lower engagement surfaces 50, 52 of the implant body 22 and the bone growth material 130 positioned therein in close proximity to the spongy cancellous bone tissue of the vertebral bodies $V_U$, $V_L$ to promote fusion. Following preparation of the vertebral endplates, the implant 20 is inserted into the disc space using a suitable insertion technique such as, for example, impaction or push-in type insertion. Notably, since the intervertebral implant 20 is inserted into the disc space while in a non-expanded configuration having an initial maximum height $h_1$ that is somewhat less than the disc space height, over distraction of the disc space is avoided and neural distraction is minimized.

In a further embodiment of the invention, the intervertebral implant 20 may be inserted into the disc space in a minimally invasive manner (i.e., through a small access portal) via the use of endoscopic equipment, a small diameter tube or cannula, or by other minimally invasive surgical techniques. However, it should be understood that the implant 20 may be inserted into the disc space using conventional surgical methods and techniques. Following insertion of the implant 20 into the disc space, the implant body 22 is expanded to the configuration illustrated in FIG. 8 (having an expanded height $h_2$) to restore and/or maintain a desired disc space height. As discussed above, transitioning of the implant body 22 to the expanded configuration results in outward deformation of the upper and lower walls 30, 32 from the inwardly curved or concave configuration illustrated in FIG. 7 to the outwardly curved or convex configuration illustrated in FIG. 8.

Figure 9:
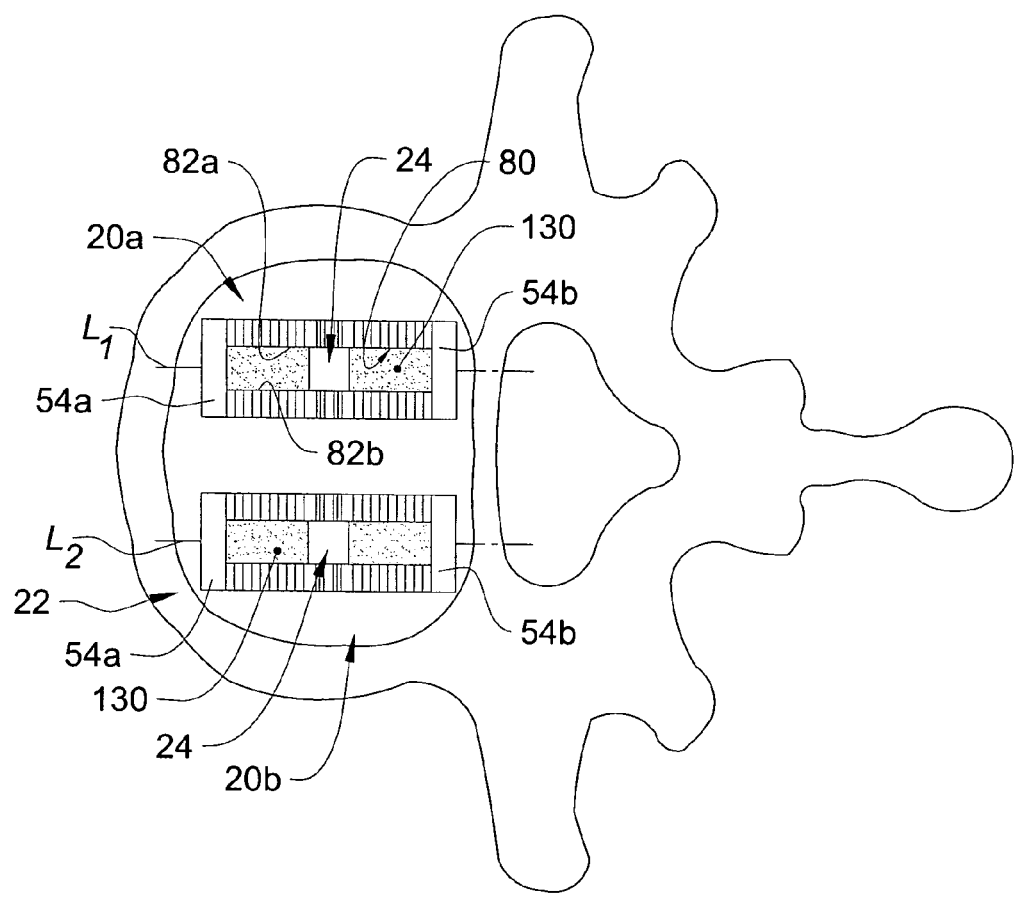
FIG. 9 is a top plan view of a pair of the expandable intervertebral implants illustrated in FIG. 1, as shown in a fully expanded state within the intervertebral disc space.

As should be appreciated, a vertebra is comprised of a hard cortical bone material extending about the outer region of the vertebral body, and a softer cancellous or spongiose bone material within of the cortical bone material. As illustrated in FIGS. 8 and 9, the upper and lower anterior/posterior bearing surfaces 54a, 54b and 56a, 56b of the implant body 22 are positioned to bear against the cortical rim/apophyseal ring region of the respective upper and lower vertebral bodies $V_U$, $V_L$ to resist the compressive forces exerted onto the implant body 22 and to reduce the likelihood of subsidence into the relatively softer cancellous or spongiseum bone tissue. Additionally, transitioning of the intervertebral implant 20 to the expanded configuration illustrated in FIG. 8 imbeds or impacts the teeth 60 extending from the upper and lower engagement surfaces 50, 52 into the vertebral endplates to resist migration and possible expulsion of the implant body 22 from the disc space. Moreover, positioning of the outwardly deformed upper and lower walls 30, 32 within the concave surface curvature C defined by the upper and lower vertebral bodies $V_U$, $V_L$ tends to increase stability of the implant body 22 and also reduces the likelihood of migration and possible expulsion of the implant body 22 from the disc space. Furthermore, positioning of the outwardly deformed upper and lower walls 30, 32 in close proximity to or in direct contact with the cancellous or spongiseum bone tissue of the upper and lower vertebral bodies $V_U$, $V_L$ facilitates bone growth into the grooves 62 and/or through the slot 80 and into the inner chamber 40.

In a further aspect of the invention, positioning of the expansion member 24 within the center compartment 90c of the inner chamber 40 provides additional support and rigidity to the upper and lower walls 30, 32 of the implant body 22 to resist compression loads from the vertebral bodies $V_U$, $V_L$, particularly near the central portion 22c of the implant body 22 which is otherwise devoid of internal support members. Additionally, as discussed above, the relatively close fitting engagement of the upper and lower segments 108a, 108b of the expansion member 24 within the slot 80 in the upper and lower walls 30, 32 also provides additional support and rigidity to the implant body 22, and particularly resists side-to-side or lateral forces exerted onto the implant 20 by the upper and lower vertebral bodies $V_U$, $V_L$. Although the intervertebral implant 20 is maintained in the expanded configuration solely via engagement between the expansion member 24 and the upper and lower walls 30, 32 of the implant body 22, it should be understood that one or more supplemental internal fixation elements may also be used to provide further support to the implant body 22, particularly in instances involving excessive vertebral loading and/or instability. It should also be understood that supplemental external intravertebral fixation elements and/or stabilization techniques may also be used if excessive residual instability is encountered following insertion and expansion of one or more of the implants 20 within the disc space.

Referring to FIG. 9, in a further embodiment of the invention, a pair of intervertebral implants 20a, 20b may be positioned side-by-side in a bilateral arrangement within the disc space. However, it should be understood that unilateral placement or central placement of a single intervertebral implant 20 within the disc space is also contemplated as falling within the scope of the present invention. Bone graft, morselized autograft bone, or a bone growth promoting substance may be positioned within the area between the implants 20a, 20b to further facilitate fusion between the upper and lower vertebral bodies $V_U$, $V_L$.

Figures 12, 13:
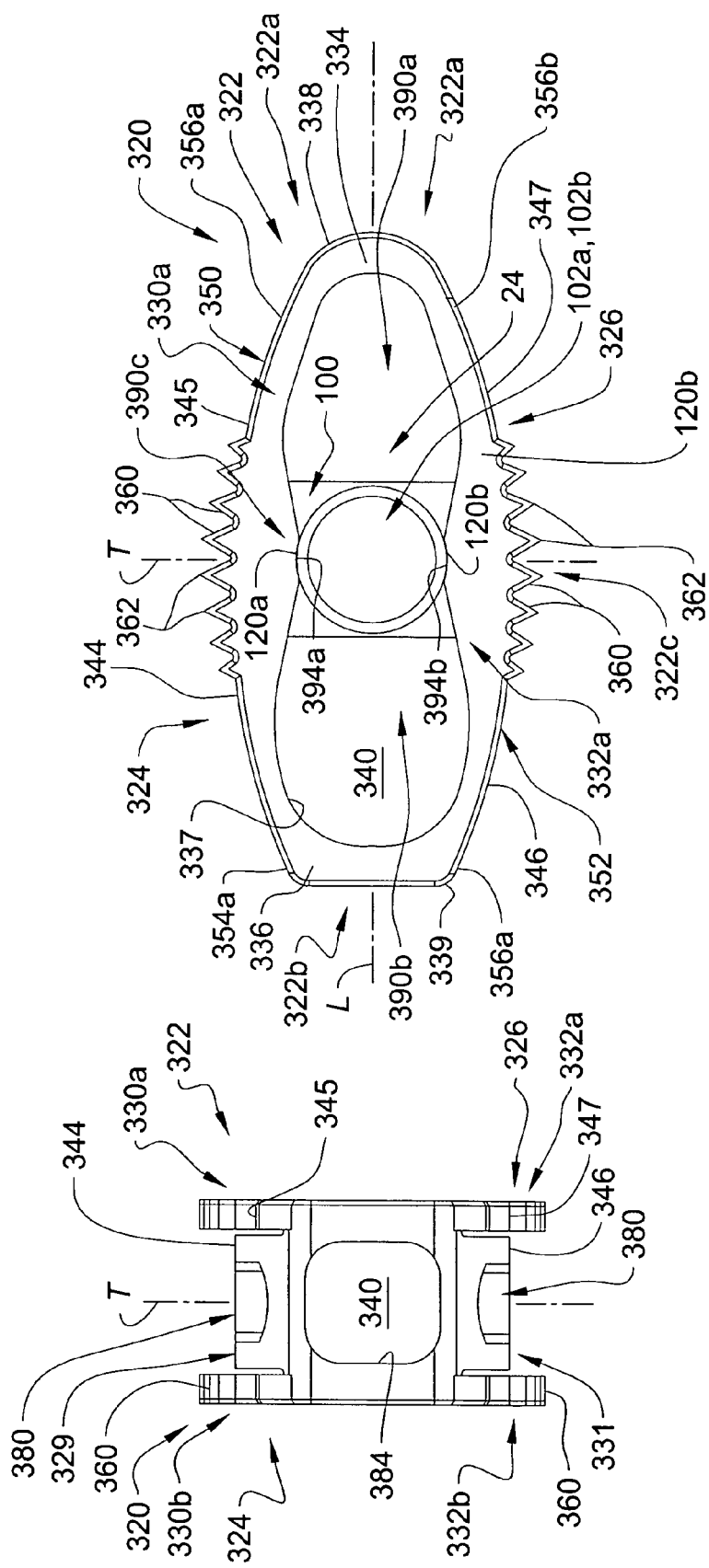
FIG. 12 is a side elevational view of the expandable spinal implant illustrated in FIG. 10, as shown in a fully expanded state.
FIG. 13 is an end elevational view of the expandable spinal implant illustrated in FIG. 10, as shown in the fully expanded state.

Referring to FIGS. 10-13, shown therein is an expandable spinal implant 320 according to another form of the present invention. The spinal implant 320 extends along a longitudinal axis L and is generally comprised of an implant body 322 and an expansion member 24. The expansion member 24 is substantially identical to the expansion member illustrated in FIGS. 5 and 6 and described above with regard to the expandable intervertebral implant 20. However, it should be understood that other types and configurations of expansion members are also contemplated for use in association with the spinal implant 320. The expansion member 24 serves to transition the implant body 322 from an initial, non-expanded state (as shown in FIGS. 10 and 11) to an expanded state (as shown in FIGS. 12 and 13), wherein expansion of the implant body 322 occurs generally along a transverse axis T. The expansion member 24 may also allow the implant body 322 to be retracted from the expanded state back toward the initial, non-expanded state. Further details regarding the features and operation of the expandable spinal implant 320 will be set forth below.

The components of the expandable spinal implant 320 are formed of a bio-compatible material. In one embodiment of the invention, the components of the spinal implant 320 are formed of a metallic material such as, for example, stainless steel and stainless steel alloys, titanium and titanium alloys, shape-memory alloys, cobalt chrome alloys, or any other suitable metallic material. In another embodiment of the invention, the components of the spinal implant 320 are formed of a non-metallic material such as, for example, a polymeric material, a ceramic material, a reinforced composite material, bone, a bone substitute material, or any other suitable non-metallic material. In the illustrated embodiment of the invention, the implant body 322 is configured as an expandable fusion cage including features that facilitate or promote bone growth into and through the implant 320 to achieve arthrodesis between the adjacent vertebral bodies, the details of which will be discussed below. However, it should be understood that in other embodiments of the invention, the implant body 322 may be configured as an expandable spacer or plug.

In one embodiment of the invention, the implant body 322 is comprised of upper and lower axial walls 324, 326 extending generally along the longitudinal axis L and spaced apart along transverse axis T, and a pair of end walls 334, 336 extending transversely between and interconnecting opposing end portions of the upper and lower walls 324, 326. In the illustrated embodiment of the invention, the upper axial wall 324 includes a central wall portion 329 and a pair of outer wall portions 330a, 330b positioned on either side of and laterally offset from the central wall portion 329, with the central wall portion 329 and the outer wall portions 330a, 330b extending along substantially an entire length of the upper axial wall 324. Similarly, the lower axial wall 326 includes a central wall portion 331 and a pair of lower outer wall portions 332a, 332b positioned on either side of and laterally offset from the central wall portion 331, with the central wall portion 331 and the outer wall portions 332a, 332b extending along substantially an entire length of the upper axial wall 326. As will be discussed in greater detail below, in the illustrated embodiment of the invention, the expansion member 24 co-acts with the upper and lower pairs of outer wall portions 330a, 330b and 332a, 332b to displace the outer wall portions in an outward direction relative to one another to provide for outward expansion of the implant body 322 generally along the transverse axis T from the initial, non-expanded state illustrated in FIGS. 10 and 11 to the expanded state illustrated in FIGS. 12 and 13, with the central upper and lower wall portions 329, 331 remaining in a substantially undeformed and stationary configuration.

However, other embodiments of the invention are also contemplated wherein the expansion member 24 co-acts with the upper and lower central wall portions 329, 331 to displace the central wall portions 329, 331 in an outward direction relative to one another to provide for outward expansion of the implant body 322 generally along the transverse axis T, with the upper and lower pairs of outer wall portions 330a, 330b and 332a, 332b remaining in a substantially stationary position. In still other embodiments of the invention, the upper axial wall 324 may include a single movable wall portion 330 positioned laterally adjacent the stationary wall portion 329, and the lower axial wall 326 may include a single movable wall portion 332 positioned laterally adjacent the stationary wall portion 331. Additionally, it should be understood that other arrangements and configurations of movable and stationary wall portions are also contemplated as falling within the scope of the present invention. It should also be understood that the term "stationary" does not necessarily require that the stationary wall portion remains in an absolute stationary position, but only requires that the stationary wall portion remain in a substantially stationary position, or that the stationary wall portion is outwardly displaced or expanded to a lesser degree compared to that of an adjacent movable wall portion.

In the illustrated embodiment of the invention, the upper and lower axial walls 324, 326 and the transverse end walls 334, 336 cooperate to define an inner chamber 340 extending generally along the longitudinal axis L. In one embodiment of the implant body 322, the upper and lower axial wall portions 324, 326 and the transverse end walls 334, 336 provide the implant body 322 with a generally rectangular axial cross-section. However, it should be understood that other shapes and configurations of the implant body 322 are also contemplated as falling within the scope of the present invention. In one aspect of the invention, the upper and lower pairs of movable wall portions 330a, 330b and 332a, 332b are coupled to the transverse end walls 334, 336 in a manner that allows the upper and lower movable wall portions to be outwardly deformed relative to one another via the expansion member 24. In one embodiment, such outward deformation is primarily attributable to the flexible nature of the upper and lower pairs of movable wall portions 330a, 330b and 332a, 332b and/or the flexible interconnection between the movable wall portions and the transverse end walls 334, 336.

In one embodiment of the invention, the upper and lower axial walls 324, 326 are formed integral with the transverse end walls 334, 336 to define a unitary, single-piece implant body 322. However, it is also contemplated that one or more portions of the axial walls 324, 326 and the transverse end walls 334, 336 may be formed separately and connected together to form a multi-piece expandable implant body assembly. As shown in FIG. 10, in a further embodiment of the invention, the interconnection location between the upper and lower pairs of the movable wall portions 330a, 330b and 332a, 332b and the transverse end walls 334, 336 include rounded inner surfaces 337 to provide increased flexibility to facilitate outward deformation of the movable wall portions during expansion of the implant body 322. Additionally, the upper and lower axial walls 324, 326 and the leading or front end wall 334 cooperate with one another to define a rounded or bullet-shaped distal end portion 338 to facilitate insertion of the implant body 322 between adjacent vertebral bodies and into the intervertebral disc space. The interconnection location between the upper and lower axial walls 324, 326 and the trailing end wall 336 also define rounded corners 339 to aid in possible removal of the implant body 322 from the intervertebral disc space and/or to minimize injury or trauma to adjacent tissue.

In a further aspect of the invention, as illustrated most clearly in FIG. 10, when in an initial, non-expanded state, the upper and lower pairs of movable wall portions 330a, 330b and 332a, 332b are recessed below the outer surfaces 344, 346 of the upper and lower axial walls 324, 326 (e.g., positioned below the outer surfaces of the upper and lower stationary wall portions 329, 331). Accordingly, when in the non-expanded state, the movable wall portions 330a, 330b and 332a, 332b define recessed regions 348 that extend inwardly along the transverse axis T relative to the outer surfaces 344, 346. In the illustrated embodiment, the recessed regions 348 provided by the movable wall portions 330a, 330b and 332a, 332b define outwardly extending convex curvatures. However, in other embodiments of the invention, the recessed regions 348 may define inwardly extending concave curvatures or may take on substantially planar configurations. Other suitable configurations and arrangements of the implant body 322 are also contemplated wherein the upper and lower pairs of movable wall portions 330a, 330b and 332a, 332b are recessed or positioned below the outer surfaces 344, 346 of the upper and lower axial walls 324, 326.

As will be discussed in greater detail below, the recessed regions 348 defined by the upper and lower pairs of movable wall portions 330a, 330b and 332a, 332b (relative to the upper and lower stationary walls 329, 331) provide the spinal implant 320 with a lower overall vertical profile to facilitate insertion of the implant 320 into the intervertebral disc space without having to distract the adjacent vertebrae apart to accommodate for the additional height that would otherwise be presented by teeth or other surface projections extending from the pairs of movable wall portions 330a, 330b and 332a, 332b. However, once the spinal implant 320 is inserted into the disc space, expansion of the implant body 322 causes outward deformation of the upper and lower movable wall portions 330a, 330b and 332a, 332b wherein the recessed regions 348 are outwardly expanded generally along the transverse axis T.

Figure 14:
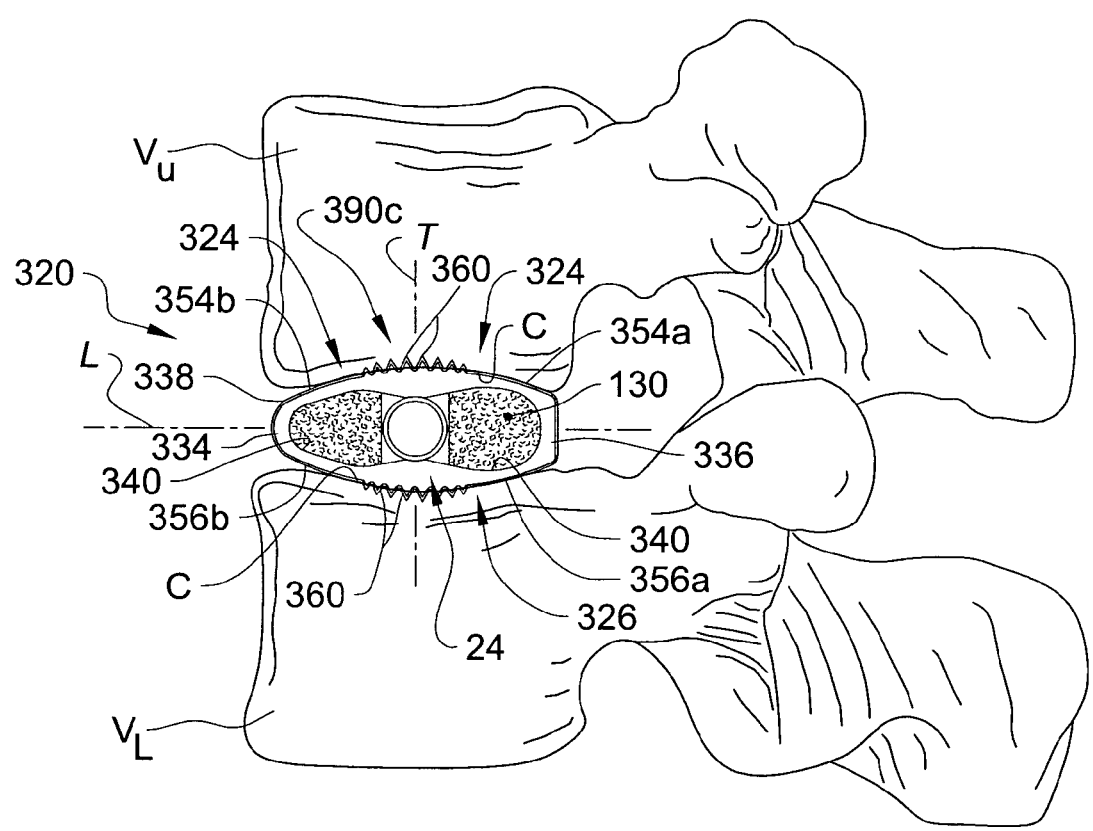
FIG. 14 is a side elevational view of the expandable spinal implant illustrated in FIG. 10, as shown in a fully expanded state within an intervertebral disc space.

In the illustrated embodiment, expansion of the implant body 322 provides each of the upper and lower movable wall portions 330a, 330b and 332a, 332b with a convex curvature that substantially corresponds to the convex curvature of the upper and lower surfaces 344, 346 defined by the stationary wall portions 329, 331. In other words, as illustrated in FIG. 12, when the spinal implant 320 is transitioned to the expanded state, the upper and lower surfaces 345, 347 of the movable wall portions are substantially aligned with the upper and lower surfaces 344, 346 of the stationary wall portions to provide the implant body 322 with upper and lower engagement surfaces 350, 352. However, other configurations are also contemplated as falling within the scope of the present invention. As will be discussed below, when the spinal implant 320 is transitioned to the expanded state, the convex curvature defined by the upper and lower engagement surfaces 350, 352 substantially corresponds to a concave surface curvature C defined by the endplates of the adjacent vertebral bodies (FIG. 14).

In one embodiment of the invention, the end portions of the implant body 322 define a pair of upper bearing surfaces 354a, 354b and a pair of lower bearing surfaces 356a, 356b adjacent the transverse end walls 334, 336. As will be discussed below, the upper and lower bearing surfaces 354a, 354b and 356a, 356b contact and bear against the cortical rim/apophyseal ring region of the respective upper and lower vertebral bodies $V_U$, $V_L$ (FIG. 14) to provide support and resistance to a substantial amount of the compressive forces exerted onto the implant body 322. In the illustrated embodiment of the invention, the upper and lower bearing surfaces 354a, 354b and 356a, 356b are substantially smooth and devoid of any steps, protrusions, projections or irregularities. However, it should be understood that in other embodiments, the upper and lower bearing surfaces may define anchoring features to aid in engaging and gripping vertebral bone.

In a further embodiment of the invention, the upper and lower movable wall portions 330a, 330b and 332a, 332b define a number of anchor elements positioned between the upper and lower bearing surfaces 354a, 354b and 356a, 356b. The anchor elements are adapted for engagement with the adjacent vertebral bodies $V_U$, $V_L$ to prevent or inhibit movement of the implant body 322 and/or to facilitate bone growth onto the implant body 322 subsequent to implantation within the intervertebral disc space (FIG. 14). In one embodiment, the anchor elements comprise a number of teeth or surface protrusions 360 projecting outwardly from the upper and lower movable wall portions 330a, 330b and 332a, 332b. However, other types and configurations of anchor elements are also contemplated including, for example, spikes, threads, ridges, bumps, surface roughening, or any other element or feature suitable for anchoring to vertebral tissue. Additionally, anchor elements comprising grooves or surface depressions formed in the upper and lower surfaces 345, 347 of the movable wall portions are also contemplated as falling within the scope of the present invention. It should also be understood that in other embodiments of the invention, the upper and lower surfaces 345, 347 need not necessarily include any anchor elements, but may alternatively have a substantially smooth configuration. Moreover, although the upper and lower surfaces 344, 346 of the stationary wall portions 329, 331 are illustrated as having a substantially smooth configuration (i.e., devoid of any surface projections or surface depressions), it should be understood that in other embodiments of the invention, the upper and lower surfaces 344, 346 may be provided with one or more types of anchor elements adapted for engagement with the adjacent vertebral bodies.

As indicated above, when the implant body 322 is in the initial, non-expanded state shown in FIG. 10, the upper and lower movable wall portions 330a, 330b and 332a, 332b define recessed regions 348 that extend inwardly along the transverse axis T so as to position the tips or peaks 362 of the teeth 360 at or below the outer surfaces 344, 346 of the upper and lower stationary walls 329, 331. However, other embodiments are also contemplated wherein the recessed regions 348 position the teeth 360 partially below the outer surfaces 344, 346 of the upper and lower stationary walls 329, 331, with the tips or peaks 362 of the teeth 360 remaining above the outer surfaces 344, 346. The recessed positioning of the teeth 360 provides the spinal implant 320 with a lower overall vertical profile to facilitate insertion into the intervertebral disc space. However, as shown in FIG. 14, upon transitioning of the implant body 322 to the expanded configuration, the teeth 360 are engaged/impacted into the vertebral endplates of the adjacent vertebral bodies $V_U$, $V_L$ to prevent or inhibit movement of the implant body 322 and possible expulsion from the disc space.

As should be appreciated, when the implant 320 is in the initial, non-expanded state (FIG. 10), the maximum non-expanded height $h_1$ of the implant body 322 is defined by the distance between the outer surfaces 344, 346 of the upper and lower stationary walls 329, 331. In order to minimize distraction of the upper and lower vertebral bodies $V_U$, $V_L$ and avoid over distraction of the disc space, the maximum non-expanded initial height $h_1$ of the implant body 322 is preferably selected to correspond to the natural disc space height. In one embodiment, the non-expanded initial height $h_1$ of the implant body 322 closely corresponds to the natural disc space height adjacent the cortical rim/apophyseal ring region adjacent the anterior/posterior portions of the upper and lower vertebral bodies $V_U$, $V_L$. However, other non-expanded initial heights $h_1$ of the implant body 322 are also contemplated as falling within the scope of the present invention.

Since the teeth 360 preferably do not protrude or extend beyond the outer surfaces 344, 346 of the stationary wall portions 329, 331, the teeth 360 do not interfere with the upper and lower vertebral bodies $V_U$, $V_L$ which could potentially impede placement of the implant 320 during insertion into the intervertebral disc space. Additionally, distraction of the upper and lower vertebral bodies $V_U$, $V_L$ to accommodate for the additional height of the teeth 360 above the outer surfaces 344, 346 is substantially avoided. Specifically, the upper and lower vertebral bodies $V_U$, $V_L$ only need to be spread apart a distance to provide a disc space height $h_d$ that is equal to or slightly greater than the maximum non-expanded height $h_1$ of the implant body 322. Additionally, the recessed positioning of the teeth 360 allow the implant body 322 to be provided with teeth 360 (or other types of surface projections) having a greater height than would otherwise be allowed for if the teeth 360 were not at least partially recessed below the stationary outer surfaces 344, 346 when the implant 320 is in the initial, non-expanded state.

In the illustrated embodiment of the implant body 322, the teeth 360 are arranged in rows extending laterally across the width of the movable wall portions 330a, 330b and 332a, 332b. Although the implant body 322 is shown as having eight rows of teeth 360 associated with each of the movable wall portions, it should be understood that the inclusion of a single row of teeth or any number of rows of teeth are also contemplated. Additionally, it should be understood that the teeth 360 may be orientated in other directions such as, for example, in a direction parallel with the longitudinal axis L or arranged at an oblique angle relative to the longitudinal axis L. In one embodiment, the teeth 360 have a triangular-shaped configuration; however, other shapes and configurations of teeth are also contemplated as falling within the scope of the present invention. Furthermore, in the illustrated embodiment of the invention, the outer teeth 360 located farthermost from the central transverse axis T have a somewhat lesser height than the intermediate teeth 360 located adjacent the central transverse axis T. As should be appreciated, this variation in height ensures that each of the teeth 360 are recessed below the convexly curved outer surfaces 344, 346 defined by the upper and lower stationary walls 329, 331. However, it should be understood that other sizes and arrangements of the teeth 360 are also contemplated as falling within the scope of the present invention.

As shown in FIG. 11, in one embodiment of the invention, the implant body 322 defines a bone in-growth opening or slot 380 extending transversely therethrough in communication with the inner chamber 340 and opening onto the outer surfaces 344, 346 of the upper and lower stationary wall portions 329, 331. In the illustrated embodiment, the slot 380 extends along substantially the entire length of the implant body 322 and defines a pair of longitudinally extending and oppositely facing side surfaces 382a, 382b at the location where the slot 380 extends through each of the stationary wall portions 329, 331. As should be appreciated, the bone in-growth slot 380 permits bone growth from the adjacent vertebral bodies and into and potentially through the implant body 322. Additionally, the slot 380 is also sized to receive a portion of the expansion member 24 therein, between the opposing side surfaces 382a, 382b, to aid in guiding the expansion member 24 generally along the longitudinal axis L to substantially prevent side-to-side displacement as the expansion member 24 is axially displaced through the implant body 322 during expansion of the spinal implant 320.

Although the implant body 322 is illustrated as having a single bone in-growth slot 380 extending transversely through and along substantially the entire length 1 of the implant body 322, it should be understood that the implant body 322 may be configured to have any number of bone in-growth slots, including two or more bone in-growth slots or openings positioned at various locations along the length of the implant body 322. Additionally, although the bone in-growth slot 380 is illustrated as having a generally rectangular configuration having a slot length extending along substantially the entire length of the implant body 322, and a slot width $w_s$ extending across about one-third of the width w of the implant body 322, it should be understood that other shapes, configurations and sizes of bone in-growth openings are also contemplated. It should further be understood that although the bone in-growth slot 380 is illustrated and described as communicating with the inner chamber 340, in other embodiments, the slot 380 need not necessarily extend entirely through the upper and lower stationary wall portions 329, 331, but may instead extend partially therethrough.

As shown in FIG. 11, in the illustrated embodiment of the implant body 322, an axial opening 384 extends through the trailing end wall 336 and into communication with the inner chamber 340. However, the rounded leading end wall 334 is preferably solid or closed off. Nevertheless, in other embodiments of the invention, an axial opening may also extend through the leading end wall 334 and into communication with the inner chamber 340. The axial opening 384 extending through the trailing end wall 336 is sized to receive an end portion of an instrument therein for engagement with the expansion member 24 to facilitate transitioning of the implant body 322 to an expanded configuration. In the illustrated embodiment of the invention, the axial opening 384 has a generally rectangular configuration and has a relatively large size which encompasses a substantially portion of the trailing end 336. However, it should be understood that other sizes, shapes and configurations of the axial opening 384 are also contemplated as falling within the scope of the present invention.

As illustrated in FIG. 10, in one embodiment of the invention, the inner chamber 340 includes a number of distinct compartments or sections positioned along the length of the implant body 322. In the illustrated embodiment of the implant body 322, the inner chamber 340 includes end compartments 390a and 390b positioned adjacent the end portions 322a and 322b of the implant body 322, and an intermediate or center compartment 390c positioned adjacent the central portion 322c of the implant body 322. However, it should be understood that the inner chamber 340 may include any number of compartments, including a single compartment, two compartments, or four or more compartments. In the illustrated embodiment of the invention, each of the chamber compartments 390a, 390b, 390c extends laterally through the entire width w of the implant body 322, thereby providing increased flexibility for expansion of the implant body 322 and also providing the implant body 322 with open sides to permit bone growth into the inner chamber 340 from lateral directions.

In the illustrated embodiment of the implant body 322, the end compartments 390a, 390b each have a tapered region wherein the inner surfaces of the upper and lower movable wall portions 330a, 330b and 332a, 332b adjacent the intermediate compartment 390c taper inwardly toward one another to define a pair of opposing ramped surfaces 392a, 392b. The center compartments 390c has an arcuate configuration, with the inner surfaces of the movable wall portions 330a, 330b and 332a, 332b defining a pair of opposing concave surfaces 394a, 394b having substantially the same curvature as the upper and lower arcuate engagement surfaces 120a, 120b defined by the expansion member 24, the details of which will be discussed below. The point of intersection between the ramped surfaces 392a, 392b of the end compartments 390a, 390b and the concave surfaces 394a, 394b of the center compartment 390c defines opposing apices or vertices 396a, 396b and 398a, 398b positioned on either side of the center compartment 390c. Although the illustrated embodiment of the implant body 322 depicts the inner chamber 340 and the compartments 390a, 390b and 390c as having a particular shape and configuration, it should be understood that other suitable shapes and configurations are also contemplate as falling within the scope of the present invention.

As indicated above, the expansion member 24 is identical to the expansion member illustrated in FIGS. 5 and 6 and as described above with regard to the intervertebral implant 20. In general, the expansion member 24 includes a central portion 100 having a generally rectangular or square cross section, and a pair of side portions 102a, 102b projecting laterally from the central portion 100 and having a generally circular cross section. At least the upper and lower segments 108a, 108b of the central portion 100 define a width $w_e$ between the side surfaces 106a, 106b that closely corresponds to the width $w_s$ of the slot 380 extending through the implant body 322. The upper and lower segments 108a, 108b of the central portion 100 are displaceable through the slot 380 and along the opposing side surfaces 382a, 382b as the expansion member 24 is axially displaced through the inner chamber 340 during transitioning of the implant body 322 toward the expanded configuration illustrated in FIGS. 12 and 13. The central portion 100 defines a passage 110 having a diameter $d_1$ and which is sized to receive a distal end portion of a surgical instrument therein such as, for example, the surgical instrument 200 shown in FIG. 7 and described above.

In the illustrated embodiment of the invention, each of the side portions 102a, 102b of the expansion member 24 defines upper and lower engagement surfaces 120a, 120b having a curved or arcuate configuration. The curved engagement surfaces 120a, 120b facilitate sliding movement along the ramped surfaces 392a, 392b of the upper and lower movable wall portions 330a, 330b and 332a, 332b of the implant body 322 as the expansion member 24 is axially displaced through the inner chamber 340 during transitioning of the implant body 322 to the expanded configuration. Additionally, the side portions 102a, 102b provide the expansion member 24 with an overall width that is less than or equal to the overall width w of the implant body 322 so that the side portions 102a, 102b do not extend laterally beyond the side surfaces of the implant body 322.

In one embodiment of the invention, the surgical instrument 200 illustrated in FIG. 7 and described above in association with the expandable implant 20 is also used to aid in the insertion of the implant 320 into the disc space and to transition the implant body 322 to the expanded configuration illustrated in FIGS. 12 and 13. However, it should be understood that other suitable types and configurations of surgical instruments are also contemplated for use in association with the present invention. The surgical instrument 200 cooperates with the spinal implant 320 in a manner very similar to that described above with regard to the spinal implant 20. Accordingly, the specific details regarding use of the surgical instrument 200 in association with the spinal implant 320 need not be discussed herein.

As shown in FIG. 10, in one embodiment of the invention, the expansion member 24 is initially positioned in the end compartment 390a adjacent the leading or distal end 322a of the implant body 322, and expansion of the implant body 322 is accomplished by pulling the expansion member 24 toward the trailing or proximal end 322b of the implant body 322 until the expansion member 24 is positioned within the center compartment 390c. In another embodiment of the invention, the expansion member 24 may be initially positioned in the end compartment 390b adjacent the proximal end 322b, with expansion of the implant 320 resulting from pushing the expansion member 24 toward the distal end 322a until the expansion member 24 is positioned within the center compartment 390c. However, the initial positioning the expansion member 24 in the distal end compartment 390a and pulling the expansion member 24 into the center compartment 390c results in the relatively simpler overall design of a "pull" style instrument, such as the surgical instrument 200 illustrated in FIG. 7 and described above.

As should be appreciated, axial displacement of the expansion member 24 in the direction of arrow A will correspondingly transition the implant body 322 toward the fully expanded configuration illustrated in FIGS. 12 and 13. More specifically, axial displacement of the expansion member 24 from the distal end compartment 390a toward the center compartment 390c slidably engages the upper and lower engagement surface 120a, 120b defined by the side portions 102a, 102b of the expansion member 24 along the opposing ramped surfaces 392a, 392b defined by the implant body 322. As a result, the upper and lower movable wall portions 330a, 330b and 332a, 332b of the implant body 322 are driven away from one another and are outwardly deformed along the transverse axis T to transition the implant body 322 from the initial, non-expanded configuration illustrated in FIGS. 10 and 11 toward the expanded configuration illustrated in FIGS. 12 and 13. The expansion member 24 is further displaced in an axial direction until positioned within the center compartment 390c of the inner chamber 340, with the side portions 102a, 102b of the expansion member 24 positioned within the recessed areas formed by the opposing concave surfaces 394a, 394b and captured between the opposing apices/vertices 396a, 396b and 398a, 398b.

It should be appreciated that positioning of the side portions 102a, 102b of the expansion member 24 within the opposing concave surfaces 394a, 394b and between the opposing apices/vertices 396a, 396b and 398a, 398b retains the expansion member 24 within the center compartment 390c and resists or inhibits further axial displacement of the expansion member 24 to thereby maintain the implant body 322 in the expanded configuration shown in FIGS. 12 and 13, even after the surgical instrument 200 is detached from the expansion member 24. It should also be appreciated that during expansion of the implant body 322, once the expansion member 24 is positioned beyond the pair of opposing apices/vertices 396a, 396b and enters or "clicks" into the center compartment 390c, the amount of linear driving force required to displace the expansion member 24 will significantly and abruptly decrease. This abrupt drop-off in driving force provides the surgeon with a perceptible indication that the expansion member 24 is properly positioned within the center compartment 390c and that the desired amount of expansion has been attained.

Additionally, as indicated above, the upper and lower segments 108a, 108b of the expansion member 24 define a width $w_e$ between the side surfaces 106a, 106b that closely corresponds to the width $w_s$ of the slot 380 extending through the implant body 322. Accordingly, as the expansion member 24 is displaced through the inner chamber 340 of the implant body 322 to transition the implant body 322 toward the expanded configuration, the upper and lower segments 108a, 108b of the central portion 100 are displaced through the slot 380, with the side surfaces 106a, 106b being slidably displaced along the opposing side surfaces 382a, 382b of the slot 380. Displacement of the upper and lower segments 108a, 108b of the central portion 100 through the slot 380 aids in guiding the expansion member 24 through the inner chamber 340 during expansion of the implant body 322. Additionally, the relatively close fit between the side surfaces 106a, 106b of the expansion member 24 and the opposing side surfaces 382a, 382b of the slot 380 provides additional support and rigidity to the implant body 322, and particularly resists side-to-side or lateral forces exerted onto the implant 320 by the upper and lower vertebral bodies $V_U$, $V_L$.

As shown in FIGS. 12 and 13, expansion of the implant body 322 increases the overall height of the upper and lower movable wall portions 330a, 330b and 332a, 332b adjacent the central portion 322c to an expanded height that is substantial equal to the height adjacent the central portion of the intervertebral disc space. As should be appreciated, the difference between the initial and expanded heights of the movable wall portions corresponds to the difference between the diameter $d_1$ (or height) of the side portions 102a, 102b of the expansion member 24 (FIGS. 5 and 6) and the non-expanded distance between the concave surfaces 394a, 394b of the center compartment 390c of the implant body 322 (FIG. 10). Accordingly, expansion of the implant body 322 can be easily and accurately controlled by providing the expansion member 24 with side portions 102a, 102b having a select diameter $d_1$ (or height) and/or by providing the center compartment 390c with a configuration having a select non-expanded distance between the concave surfaces 394a, 394b.

When the implant body 322 is transitioned to the expanded configuration, the upper and lower movable wall portions 330a, 330b and 332a, 332b are outwardly deformed away from one another along the transverse axis T to increase the overall height thereof. Since the end portions of the upper and lower movable wall portions 330a, 330b and 332a, 332b are integrally connected to the end walls 334, 336, the end portions of the movable wall portions remain relatively stationary, and expansion of the implant body 322 adjacent the implant end portions 322a, 322b is limited. However, since the central portions of the upper and lower movable wall portions 330a, 330b and 332a, 332b are not interconnected, expansion of the implant body 322 occurs primarily along the central portion 322c of the implant body 322. As a result, upon expansion of the implant body 322, the upper and lower movable wall portions 330a, 330b and 332a, 332b each form an outwardly extending convex curvature relative to the longitudinal axis L. As illustrated in FIG. 14, the convex curvature of the outwardly deformed movable wall portions 330a, 330b and 332a, 332b preferably substantially corresponds to the anterior-to-posterior surface curvature defined by the vertebral endplates of the adjacent vertebral bodies $V_U$, $V_L$. Additionally, expansion of the implant body 322 generally along the transverse axis T imbeds or impacts the teeth 360 extending from the upper and lower movable wall portions into the vertebral endplates to resist migration and possible expulsion of the implant body 322 from the intervertebral disc space. Following expansion of the implant body 322, the surgical instrument 200 is disengaged from the expansion member 24 and removed from the patient.

If removal of the expanded implant 320 from the disc space is required due to non-optimal placement of the implant 320 or for other reasons, the implant body 322 can be transitioned from the expanded configuration (FIG. 12) back toward the initial, non-expanded configuration (FIG. 10) by simply repositioning the expansion member 24 from the center compartment 390c to the proximal end compartment 390b. Such repositioning will in turn cause the flexible implant body 322 to retract toward the initial, non-expanded configuration illustrated in FIG. 10, wherein the teeth 360 will once again be at least partially inwardly recessed relative to the outer surfaces 344, 346 of the upper and lower stationary wall portions 329, 331 so as to avoid interfering with the upper and lower vertebral bodies $V_U$, $V_L$ which may otherwise impede removal of the implant 320 from the intervertebral disc space. The implant 320 may then be removed from the disc space and reintroduced therein using the insertion and expansion procedures outlined above to reposition the implant 320 into a revised position within the disc space.

In a further aspect of the invention, following the insertion and expansion of the implant 320 within the disc space, a bone growth promoting material 130 (FIG. 14) is loaded into the inner chamber 340 of the implant body 322 to facilitate or promote bone growth from the upper and lower vertebral bodies $V_U$, $V_L$, through the slot 380 extending through the upper and lower stationary wall portions 329, 331, and into and possibly through the implant body 322. In one embodiment of the invention, the bone growth promoting material 130 is loaded or packed into the inner chamber 340 via the axial opening 384 in the rear end wall 336 subsequent to insertion and expansion of the implant body 322. However, in an alternative embodiment, a portion of the bone growth promoting material 130 may be pre-loaded into the inner chamber 340 prior to insertion and expansion of the implant body 322.

As indicated above, the size of the passage 110 in the central portion 100 of the expansion member 24 is relatively large. As a result, the bone growth promoting material 130 may be conveyed through the large passage 110 in the expansion member 24 and into the distal end compartment 390a of the inner chamber 340. Once the distal end compartment 390a is fully loaded, additional bone growth promoting material 130 may be loaded into the proximal end compartment 390b of the inner chamber 340. As should be appreciated, due to the inclusion of the relatively large passage 110 in the expansion member 24, the bone growth promoting material 130 need not be preloaded into the distal end compartment 390a prior to insertion and expansion of the implant 320 within the disc space. Additionally, conveying the bone growth promoting material 130 through the relatively large passage 110 in the expansion member 24 allows the entire inner chamber 340 to be tightly packed with the bone growth promoting material 130. Additionally, bone graft, morselized autograft bone or a similar type of material may be positioned laterally adjacent the expanded implant body 322 to further promote fusion with the adjacent vertebral bodies $V_U$, $V_L$.

Having illustrated and described the elements and operation of the spinal implant 320, reference will now be made to a technique for implanting the spinal implant 320 within an intervertebral disc space according to one embodiment of the invention. However, it should be understood that other implantation techniques and procedures are also contemplated, and that the following technique in no way limits the scope of the present invention.

In one embodiment of the invention, access to the spinal column and insertion of the spinal implant 320 into the disc space is accomplished via a posterior surgical approach.

However, it should be understood that access and insertion of the spinal implant 320 into the disc space may be accomplished via other surgical approaches such as, for example, an anterior approach or a lateral approach. In another embodiment of the invention, the spinal implant 320 is used to treat the lumbar region of the spine, with the upper and lower vertebral bodies $V_U$, $V_L$ comprising lumbar vertebral bodies. However, it should be understood that the present invention is also applicable to other portions of the spine such as, for example, the cervical, thoracic or sacral regions of the spinal column. Initially, the portion of the spinal column to be treated is identified and accessed from a posterior approach using known surgical techniques. At least a portion of the natural intervertebral disc is removed via a total or partial discectomy to provide an opening for receiving the spinal implant 320 between the upper and lower vertebral bodies $V_U$, $V_L$. The disc space is then distracted to a height substantially equal to the natural disc space height. Prior to insertion of the spinal implant 320, the disc space and the endplates of the upper and lower vertebral bodies $V_U$, $V_L$ may be prepared using various cutting tools and/or other types of surgical instruments (e.g., curettes, chisels, etc.).

In a further embodiment of the present invention, the cutting instrument used to prepare the vertebral bodies $V_U$, $V_L$ is adapted to cut and remove bone tissue from the vertebral endplates while substantially retaining the natural concave curvature of the endplates and avoiding cutting into the cortical rim/apophyseal ring region adjacent the anterior/posterior portions of the vertebral endplates. The cutting instrument may also be configured to collect bony debris or chips generated during the cutting operation for subsequent insertion into the inner chamber 340 of the implant body 322 to promote arthrodesis. As illustrated in FIG. 14, each of the prepared vertebral endplates defines a recessed area or surface curvature that is generally concave in an anterior-to-posterior direction. As should be appreciated, the recessed area or surface curvature defined by the vertebral bodies $V_U$, $V_L$ receives the upper and lower stationary wall portions 329, 331 of the expanded implant body 322 so as to position the bone growth material 130 positioned therein in close proximity to the spongy cancellous bone tissue of the vertebral bodies $V_U$, $V_L$ to promote fusion. Following preparation of the vertebral endplates, the implant 320 is inserted into the disc space using a suitable insertion technique such as, for example, impaction or push-in type insertion. Notably, since the spinal implant 320 is inserted into the disc space while in a non-expanded configuration having an initial maximum height $h_1$ that is somewhat less than the disc space height, over distraction of the disc space is avoided and neural distraction is minimized.

Following insertion of the implant 320 into the intervertebral disc space, the implant body 322 is expanded to the configuration illustrated in FIG. 14 to restore and/or maintain a desired disc space height. Additionally, transitioning of the spinal implant 320 to the expanded configuration illustrated in FIG. 14 imbeds or impacts the teeth 360 into the vertebral endplates to resist migration and possible expulsion of the implant body 322 from the disc space. Moreover, positioning of the outwardly deformed upper and lower movable wall portions 330a, 330b and 332a, 332b within the concave surface curvature defined by the upper and lower vertebral bodies $V_U$, $V_L$ tends to increase stability of the implant body 322 and also reduces the likelihood of migration and possible expulsion of the implant body 322 from the disc space. Furthermore, positioning of the upper and lower stationary wall portions 329, 331 in close proximity to or in direct contact with the cancellous or spongiseum bone tissue of the upper and lower vertebral bodies $V_U$, $V_L$ facilitates bone growth through the slot 380 and into the inner chamber 340. The upper and lower anterior/posterior bearing surfaces 354a, 354b and 356a, 356b of the implant body 322 are positioned to bear against the cortical rim/apophyseal ring region of the respective upper and lower vertebral bodies $V_U$, $V_L$ to resist the compressive forces exerted onto the implant body 322 and to reduce the likelihood of subsidence into the relatively softer cancellous or spongiseum bone tissue.

In a further aspect of the invention, positioning of the expansion member 24 within the center compartment 390c of the inner chamber 340 provides additional support and rigidity to the upper and lower movable wall portions 330a, 330b and 332a, 332b of the implant body 322 to resist compression loads from the vertebral bodies $V_U$, $V_L$, particularly near the central portion 322c of the implant body 322 which is otherwise devoid of internal support members. Additionally, as discussed above, the relatively close fitting engagement of the upper and lower segments 108a, 108b of the expansion member 24 within the slot 380 in the upper and lower stationary wall portions 329, 331 also provides additional support and rigidity to the implant body 322, and particularly resists side-to-side or lateral forces exerted onto the implant 320 by the upper and lower vertebral bodies $V_U$, $V_L$. Although the spinal implant 320 is maintained in the expanded configuration solely via engagement between the expansion member 24 and the upper and lower wall portions of the implant body 322, it should be understood that one or more supplemental internal fixation elements may also be used to provide further support to the implant body 322, particularly in instances involving excessive vertebral loading and/or instability. It should also be understood that supplemental external intravertebral fixation elements and/or stabilization techniques may also be used if excessive residual instability is encountered following insertion and expansion of one or more of the implants 320 within the disc space.

In a further embodiment of the invention, a pair of the expandable spinal implants 320 may be positioned side-by-side in a bilateral arrangement within the disc space in a manner similar to that shown in FIG. 9. However, it should be understood that unilateral placement or central placement of a single spinal implant 320 within the disc space is also contemplated as falling within the scope of the present invention. Bone graft, morselized autograft bone, or a bone growth promoting substance may be positioned within the area between the bilateral implants 320 to further facilitate fusion between the upper and lower vertebral bodies $V_U$, $V_L$.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An expandable spinal implant, comprising:
   an implant body having a longitudinal axis and being transitionable between an initial configuration and an expanded configuration, said implant body including first and second ends and first and second axial walls extending along a length of said implant body and spaced apart along a transverse axis extending along a height of said implant body, at least one of said axial walls including first and second axial wall portions laterally offset from one another along a width of said implant body, said first axial wall portion positioned laterally adjacent said second axial wall portion, said first and second axial wall portions extending continuously and substantially entirely along said length of said implant body from said first end to said second end and being flexibly deformable to facilitate flexible deformation of said first axial wall portion; and an expansion member co-acting with said first axial wall portion to flexibly deform said first axial wall portion and outwardly displace a central region of said first axial wall portion relative to said second axial wall portion generally along said transverse axis to transition said implant body from said initial configuration to said expanded configuration, said expansion member engaged with said central region of said first axial wall portion in said expanded configuration; and wherein said implant body includes first and second transverse end walls interconnecting opposite end portions of said first axial wall with opposite end portions of said second axial wall, and wherein said first and second axial wall portions each extend continuously from said first transverse end wall to said second transverse end wall.

2. An expandable spinal implant, comprising:

an implant body having a longitudinal axis and being transitionable between an initial configuration and an expanded configuration, said implant body including first and second ends and first and second axial walls extending along a length of said implant body and spaced apart along a transverse axis extending along a height of said implant body, at least one of said axial walls including first and second axial wall portions laterally offset from one another along a width of said implant body, said first axial wall portion positioned laterally adjacent said second axial wall portion, said first and second axial wall portions extending continuously and substantially entirely along said length of said implant body from said first end to said second end and being flexibly deformable to facilitate flexible deformation of said first axial wall portion; and an expansion member co-acting with said first axial wall portion to flexibly deform said first axial wall portion and outwardly displace a central region of said first axial wall portion relative to said second axial wall portion generally along said transverse axis to transition said implant body from said initial configuration to said expanded configuration, said expansion member engaged with said central region of said first axial wall portion in said expanded configuration.

3. The implant of claim 2, wherein said second axial wall portion remains substantially stationary relative to said first axial wall portion as said implant body is transitioned from said initial configuration to said expanded configuration.

4. The implant of claim 2, wherein said first axial wall portion is positioned proximately adjacent said second axial wall portion.

5. The implant of claim 2, wherein said first axial wall portion defines a recessed region relative to said second axial wall portion when said implant body is in said initial configuration; and wherein said recessed region is outwardly expanded generally along said transverse axis as said implant body is transitioned from said initial configuration to said expanded configuration.

6. The implant of claim 2, wherein said at least one of said axial walls includes a third axial wall portion laterally offset from said second axial wall portion with said first and third axial wall portions positioned on opposite sides of said second axial wall portion; and wherein said expansion member co-acts with each of said first and third axial wall portions to outwardly displace said first and third axial wall portions relative to said second axial wall portion generally along said transverse axis to transition said implant body from said initial configuration to said expanded configuration.

7. The implant of claim 6, wherein said second axial wall portion remains substantially stationary relative to said first and third axial wall portions as said implant body is transitioned from said initial configuration to said expanded configuration.

8. The implant of claim 6, wherein each of said first and third axial wall portions includes an outer surface and a number of surface protrusions projecting outwardly therefrom, said surface protrusions at least partially positioned inward of an outer surface of said second axial wall portion when said implant body is in said initial configuration.

9. The implant of claim 2, wherein said first axial wall portion includes a first outer surface that is inwardly recessed relative to a second outer surface of said second axial wall portion when said implant body is in said initial configuration.

10. The implant of claim 9, wherein said first outer surface of said first axial wall portion is substantially aligned with said second outer surface of said second axial wall portion when said implant body is transitioned to said expanded configuration.

11. The implant of claim 9, wherein said first axial wall portion includes a number of surface protrusions projecting outwardly from said first outer surface, at least a portion of said surface protrusions being inwardly recessed relative to said second outer surface of said second axial wall portion when said implant body is in said initial configuration.

12. The implant of claim 11, wherein said surface protrusions comprise teeth adapted for engagement with vertebral bone.

13. The implant of claim 11, wherein said surface protrusions are entirely inwardly recessed relative to said second outer surface of said second axial wall portion when said implant body is in said initial configuration.

14. The implant of claim 11, wherein said surface protrusions are at least partially positioned outward of said second outer surface of said second axial wall portion when said implant body is transitioned to said expanded configuration.

15. The implant of claim 2, wherein one of said first and second axial wall portions defines a slot having a length extending generally along said longitudinal axis; and wherein said expansion member includes a body portion positioned within said slot and a side portion positioned between said first and second axial walls such that axial movement of said expansion member generally along said longitudinal axis displaces said body portion along said length of said slot and displaces said side portion between said axial walls to outwardly displace said first axial wall portion relative to said second axial wall portion, said body portion sized for sliding engagement along opposing side surfaces of said slot to guide said expansion member generally along said longitudinal axis during said axial movement.

16. The implant of claim 15, wherein said at least one of said axial walls includes a third axial wall portion laterally offset from said second axial wall portion with said first and third axial wall portions positioned on opposite sides of said second axial wall portion; and wherein said expansion member includes a pair of said side portions extending in generally opposite directions relative to said body portion, each of said side portions at least partially positioned between said axial walls such that axial movement of said expansion member generally along said longitudinal axis displaces said side portions of said expansion member between said axial walls to outwardly displace said first and third axial wall portions relative to said second axial wall portion generally along said transverse axis to transition said implant body from said initial configuration to said expanded configuration.

17. The implant of claim 2, wherein said implant body includes leading and trailing end portions positioned generally along said longitudinal axis, said leading end portion having a rounded outer profile to facilitate insertion into an intervertebral disc space.

18. The implant of claim 2, wherein said first axial wall portion defines a recessed region relative to said second axial wall portion when said implant body is in said initial configuration; and wherein said recessed region of said first axial wall portion is outwardly expanded generally along said transverse axis relative to said second axial wall portion as said implant body is transitioned from said initial configuration to said expanded configuration.

19. The implant of claim 18, wherein said second axial wall portion remains substantially stationary relative to said first axial wall portion as said implant body is transitioned from said initial configuration to said expanded configuration.

20. The implant of claim 18, wherein said recessed region extends along substantially an entire length of said at least one of said axial walls.

21. The implant of claim 18, wherein the first axial wall portion is positioned proximately adjacent said second axial wall portion.

22. The implant of claim 18, wherein said recessed region extends along substantially an entire length of said at least one of said axial walls between said pair of opposite end portions.

23. The implant of claim 18, wherein said first axial wall portion includes a number of surface protrusions projecting outwardly from said recessed region, at least a portion of said surface protrusions being inwardly recessed relative to an outer surface of said second axial wall portion when said implant body is in said initial configuration.

24. The implant of claim 23, wherein said surface protrusions are entirely inwardly recessed relative to said outer surface of said second axial wall portion when said implant body is in said initial configuration.

25. The implant of claim 18, wherein said recessed region defined by said first axial wall portion comprises a convex curvature extending outwardly along said transverse axis and along substantially an entire length of said at least one of said axial walls.

26. The implant of claim 18, wherein said at least one of said axial walls includes a third axial wall portion laterally offset from said second axial wall portion with said first and third axial wall portions positioned on opposite sides of said second axial wall portion, each of said first and third axial wall portions defining a corresponding one of said recessed regions when said implant body is in said initial configuration; and wherein said expansion member co-acts with each of said first and third axial wall portions to transition said implant body from said initial configuration to said expanded configuration wherein said recessed regions are outwardly expanded generally along said transverse axis.

27. The implant of claim 26, wherein said second axial wall portion remains substantially stationary relative to said first and third axial wall portions as said implant body is transitioned from said initial configuration to said expanded configuration.

28. The implant of claim 26, wherein each of said first and third axial wall portions includes a number of surface protrusions projecting outwardly from said recessed regions, at least a portion of said surface protrusions being inwardly recessed relative to an outer surface of said second axial wall portion when said implant body is in said initial configuration.

29. The implant of claim 18, wherein said first axial wall portion includes a first outer surface that is inwardly positioned relative to a second outer surface of said second axial wall portion when said implant body is in said initial configuration to define said recessed region.

30. The implant of claim 29, wherein said first outer surface of said first axial wall portion is substantially aligned with said second outer surface of said second axial wall portion when said implant body is in said expanded configuration.

31. The implant of claim 29, wherein said first axial wall portion includes a number of surface protrusions projecting outwardly from said first outer surface, at least a portion of said surface protrusions being inwardly recessed relative to said second outer surface of said second axial wall portion when said implant body is in said initial configuration.

32. The implant of claim 31, wherein said surface protrusions are entirely inwardly recessed relative to said second outer surface of said second axial wall portion when said implant body is in said initial configuration.

33. The implant of claim 2, wherein said first and second axial wall portions each extend continuously along an entire length of said implant body from said first end to said second end.

34. The implant of claim 2, wherein said first end of said implant body comprises a leading distal end portion and said second end of implant body comprises a trailing proximal end portion of said implant body, and wherein said first and second axial wall portions each extend continuously from said leading distal end portion to said trailing proximal end portion.

35. The implant of claim 2, wherein said implant body includes first and second transverse end walls, and wherein said first and second axial wall portions each extend continuously from said first transverse end wall to said second transverse end wall.

36. An expandable spinal implant, comprising:

an implant body having a longitudinal axis and being transitionable between an initial configuration and an expanded configuration, said implant body including first and second ends and first and second axial walls extending along a length of said implant body and spaced apart along a transverse axis extending along a height of said implant body, at least one of said axial walls including a movable wall portion and a substantially stationary wall portion laterally offset from one another along a width of said implant body, said movable wall portion positioned laterally adjacent said substantially stationary wall portion, said movable and stationary wall portions extending continuously and substantially entirely along said length of said implant body from said first end to said second end and being flexibly deformable to facilitate flexible deformation of said movable wall portion; and an expansion member co-acting with said movable wall portion to flexibly deform said movable wall portion and outwardly displace a central region of said movable wall portion relative to said stationary wall portion generally along said transverse axis to transition said implant body from said initial configuration to said expanded configuration, said expansion member engaged with said central region of said movable wall portion in said expanded configuration; and wherein said implant body includes first and second transverse end walls interconnecting opposite end portions of said first axial wall with opposite end portions of said second axial wall, and wherein said movable and stationary wall portions each extend continuously from said first transverse end wall to said second transverse end wall.

37. An expandable spinal implant, comprising:

an implant body having a longitudinal axis and being transitionable between an initial configuration and an expanded configuration, said implant body including first and second ends and first and second axial walls extending along a length of said implant body and spaced apart along a transverse axis extending along a height of said implant body, at least one of said axial walls including a movable wall portion and a substantially stationary wall portion laterally offset from one another along a width of said implant body, said movable wall portion positioned laterally adjacent said substantially stationary wall portion, said movable and stationary wall portions extending continuously and substantially entirely along said length of said implant body from said first end to said second end and being flexibly deformable to facilitate flexible deformation of said movable wall portion; and an expansion member co-acting with said movable wall portion to flexibly deform said movable wall portion and outwardly displace a central region of said movable wall portion relative to said stationary wall portion generally along said transverse axis to transition said implant body from said initial configuration to said expanded configuration, said expansion member engaged with said central region of said movable wall portion in said expanded configuration.

38. The implant of claim 36, wherein said movable wall portion defines a recessed region relative to said stationary wall portion when said implant body is in said initial configuration; and wherein said recessed region is outwardly expanded generally along said transverse axis as said implant body is transitioned from said initial configuration to said expanded configuration.

39. The implant of claim 37, wherein the movable wall portion is positioned proximately adjacent said stationary wall portion.

40. The implant of claim 37, wherein said at least one of said axial walls includes a pair of said movable wall portions positioned on opposite sides of said stationary wall portion; and wherein said expansion member co-acts with each of said movable wall portions to outwardly displace said movable wall portions relative to said stationary wall portion generally along said transverse axis to transition said implant body from said initial configuration to said expanded configuration.

41. The implant of claim 37, wherein said movable wall portion includes a first outer surface that is inwardly recessed relative to a second outer surface of said stationary wall portion when said implant body is in said initial configuration.

42. The implant of claim 37, wherein said implant body includes leading and trailing end portions positioned generally along said longitudinal axis, said leading end portion having a bullet-shaped configuration to facilitate insertion into an intervertebral disc space.

43. The implant of claim 37, wherein said movable and stationary wall portions each extend continuously along an entire length of said implant body from said first end to said second end.

44. The implant of claim 37, wherein said first end of said implant body comprises a leading distal end portion and said second end of implant body comprises a trailing proximal end portion of said implant body, and wherein said movable and stationary wall portions each extend continuously from said leading distal end portion to said trailing proximal end portion.

45. The implant of claim 37, wherein said implant body includes first and second transverse end walls, and wherein said movable and stationary wall portions each extend continuously from said first transverse end wall to said second transverse end wall.

* * * * *

UNITED STATES PATENT AND TRADEMARK OFFICE
CERTIFICATE OF CORRECTION

PATENT NO. : 7,655,043 B2  Page 1 of 1
APPLICATION NO. : 11/117890
DATED : February 2, 2010
INVENTOR(S) : Peterman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 339 days.

Signed and Sealed this

Twenty-third Day of November, 2010

David J. Kappos
*Director of the United States Patent and Trademark Office*